US010307411B2

(12) United States Patent
Moran et al.

(10) Patent No.: US 10,307,411 B2
(45) Date of Patent: Jun. 4, 2019

(54) USE OF COTININE IN TREATING OR PREVENTING NEUROGENESIS DEFICITS AND ENHANCING NEUROGENESIS

(71) Applicants: Department of Veterans Affairs, Washington, DC (US); University of South Florida, Tampa, FL (US)

(72) Inventors: Valentina Echeverria Moran, Largo, FL (US); Doreen Appunn, Tampa, FL (US)

(73) Assignees: THE UNITED STATES OF AMERICA AS REPRESENTED BY THE DEPARTMENT OF VETERANS AFFAIRS, Washington, DC (US); UNIVERSITY OF SOUTH FLORIDA, Tampa, FL (US)

( * ) Notice: Subject to any disclaimer, the term of this patent is extended or adjusted under 35 U.S.C. 154(b) by 13 days.

(21) Appl. No.: 15/583,937

(22) Filed: May 1, 2017

(65) Prior Publication Data

US 2017/0296525 A1 Oct. 19, 2017

Related U.S. Application Data

(63) Continuation-in-part of application No. PCT/US2015/058625, filed on Nov. 2, 2015.

(60) Provisional application No. 62/073,339, filed on Oct. 31, 2014.

(51) Int. Cl.
| | |
|---|---|
| *A61K 31/444* | (2006.01) |
| *A61K 31/454* | (2006.01) |
| *A61K 31/4545* | (2006.01) |
| *A61K 31/55* | (2006.01) |

(52) U.S. Cl.
CPC .......... *A61K 31/454* (2013.01); *A61K 31/444* (2013.01); *A61K 31/4545* (2013.01); *A61K 31/55* (2013.01)

(58) Field of Classification Search
CPC .................................................. A61K 31/444
See application file for complete search history.

(56) References Cited

U.S. PATENT DOCUMENTS

| | | | |
|---|---|---|---|
| 2008/0108574 | A1 | 5/2008 | Barlow et al. |
| 2010/0104505 | A1 | 4/2010 | Moran |

OTHER PUBLICATIONS

Akhtar, W., et al. "Association of blood cotinine level with cognitive and physical performance in non-smoking older adults." Environ Res. (Feb. 2013), vol. 121, pp. 1-16. (Year: 2013).*
MD Anderson Cancer Center. "Prevention and Treatment of Chemobrain." © 2018. Available from: < https://www.mdanderson. org/research/departments-labs-institutes/labs/neuroimmunology-laboratory/research/prevention-and-treatment-of-chemobrain.html >. (Year: 2018).*
Hatsukami, D., et al. "Cotinine: effects with and without nicotine." © Jan. 1998. Accessed Jul. 28, 2018. Psychopharmacology (Berl). vol. 135, No. 2, pp. 141-150. Available from: < https://www.ncbi.nlm.nih.gov/pubmed/9497019 >. (Year: 1998).*
Clemens, K.J., et al. "The addition of five minor tobacco alkaloids increases nicotine-induced hyperactivity, sensitization and intravenous self-administration in rats." (2009). Accessed Aug. 3, 2018. International J. Neuropsychopharmacology. vol. 12, pp. 1355-1366. (Year: 2009).*
Conway, J.R. "Smoking while on chemotherapy." © Sep. 30, 2013. Accessed Jul. 28, 2018. Available from: < https://www.oncologynurseadvisor.com/advisor-forum/smoking-while-on-chemotherapy/article/314041/ >. (Year: 2013).*
Uhl, E., et al. "Mouse Models as Predictors of Human Responses: Evolutionary Medicine." Curr. Pathobiology Rep (2015), vol. 3, pp. 219-223. (Year: 2015).*
LeSage, M.G., et al. "The Reinforcement Threshold for Nicotine as a Target for Tobacco Control." Drug Alcohol Depend. Sep. 1, 2012 vol. 125 (1-2), pp. 1-7. Accessed Jul. 28, 2018.. (Year: 2012).*
Crooks, P.A., et al. "(S)-(−)-Cotinine, the Major Brain Metabolite of Nicotine, Stimulates Nicotinic Receptors to Evoke [3H]Dopamine Release from Rat Striatal Slices in a Calcium-Dependent Manner." Journal Pharmacology Experimental Therapeutic.Accessed Jul. 30, 2018.(1999),vol. 288, No. 2, pp. 905-911. (Year: 1999).*
Chiolero, A., et al. "Consequences of smoking for body weight, body fat distribution, and insulin resistance." Am. J. Clin. Nutr. Accessed Jul. 30, 2018. (2008), vol. 87, pp. 801-809.. (Year: 2008).*
"How is Chemotherapy Given?" Chemocare.com. (Feb. 1, 2013). Accessed Jul. 29, 2018. Available from: < https://web.archive.org/web/20130201034638/http://chemocare.com/chemotherapy/what-is-chemotherapy/how-chemotherapy-is-given.aspx >. (Year: 2013).*
Iarkov, A., et al. "Post-treatment with cotinine improved memory and decreased depressive-like behavior after chemotherapy in rats." Cancer Chemother Pharmacol. (2016), vol. 78, pp. 1033-1039. (Year: 2016).*
International Search Report dated Jan. 8, 2016 in connection with the International Application No. PCT/US2015/058625 Exhibit 3 (provided concurrently by US mail), dated Nov. 2, 2015.
Barbieri RL, Gochberg J, Ryan KJ (1986) Nicotine, cotinine, and anabasine inhibit aromatase in human trophoblast in vitro. *J Clin Invest* 77(6):1727-1733 Exhibit 4 (provided concurrently by US mail).
Boyle, et al., Hostility, Anger and Depression Predict Increases in C3 over a 10-Year Period. *Brain Behav Immun*. 2007. 21 (6): 816-823. Exhibit 5 (provided concurrently by US mail).
Woods J (2011) Chemotherapy-induced cognitive impairment is associated with decreases in cell proliferation and histone modifications. BMC Neurosci 12t al., (2004) VEGF links hippocampal activity with neurogenesis, learning and memory. *Nat Genet*, 36, 827-835. Exhibit 6 (provided concurrently by US mail).

(Continued)

*Primary Examiner* — Andrew D Kosar
*Assistant Examiner* — John S Kenyon
(74) *Attorney, Agent, or Firm* — Ballard Spahr LLP

(57) ABSTRACT

A method of inhibiting or treating chemotherapy-induced cognitive dysfunction comprising administering a therapeutically effective amount of cotinine to a cancer patient experiencing chemotherapy-induced cognitive dysfunction.

18 Claims, 10 Drawing Sheets

(56) References Cited

OTHER PUBLICATIONS

Castagne V, Moser P, Roux S, Porsolt RD (2010) Rodent models of depression: forced swim and tail suspension behavioral despair tests in rats and mice. *Curr Protoc Neurosci* 49:5.8.1-5.8.14 Exhibit 7 (provided concurrently by US mail).

Christie LA, Acharya MM, Parihar VK, Nguyen A, Martirosian V, Limoli CL (2012) Impaired cognitive function and hippocampal neurogenesis following cancer chemotherapy. *Clin Cancer Res* 18(7):1954-1965 Exhibit 8 (provided concurrently by US mail).

Echeverria Moran, (2012) Cotinine: Beyond that Expected, More than a Biomarker of Tobacco Consumption. *Frontiers in pharmacology*, 3, 173. Exhibit 9 (provided concurrently by US mail).

Fabel, et al., (2003) VEGF is necessary for exercise-induced adult hippocampal neurogenesis. *Eur J Neurosci*, 18, 2803-2812 Exhibit 10 (provided concurrently by US mail).

Fardell JE, Vardy J, Johnston IN (2013) The short and long term effects of docetaxel chemotherapy on rodent object recognition and spatial reference memory. *Life Sci* 93(17):596-604 Exhibit 11 (provided concurrently by US mail).

Fournier & Duman, (2012) Role of vascular endothelial growth factor in adult hippocampal neurogenesis: implications for the pathophysiology and treatment of depression. *Behav Brain Res*, 227, 440-449 Exhibit 12 (provided concurrently by US mail).

Fuxe, et al., (1979) On the action of nicotine and cotinine on central 5-hydroxytryptamine neurons. *Pharmacol Biochem Behav*, 10, 671-677 Exhibit 13 (provided concurrently by US mail).

Grizzell JA, Iarkov A, Holmes R, Mori T, Echeverria V (2014) Cotinine reduces depressive-like behavior, working memory deficits, and synaptic loss associated with chronic stress in mice. *Behav Brain Res* 268:55-65 Exhibit 14 (provided concurrently by US mail).

Grizzell JA, Echeverria V (2014) New insights into the mechanisms of action of cotinine and its distinctive effects from nicotine. *Neurochem Res* 40:2032-2046 Exhibit 15 (provided concurrently by US mail).

Ghashghaei, et al., Reinduction of ErbB2 in astrocytes promotes radial glial progenitor identity in adult cerebral cortex, *Genes Dev.* 2007. 21 (24): 3258-3271 Exhibit 16 (provided concurrently by US mail).

Hatsukami, et al., (1997) Safety of cotinine in humans: physiologic, subjective, and cognitive effects. *Pharmacol Biochem Behav*, 57, 643-650. Exhibit 17 (provided concurrently by US mail).

Iarkov A, Appunn D, Echeverria V (2016) Post-treatment with cotinine improved memory and decreased depressive-like behavior after chemotherapy in rats. *Cancer Chemotherapy and Pharmacology*. 78(5):1033-1039. Exhibit 18 (provided concurrently by US mail).

Koppelmans V, Breteler MM, Boogerd W, Seynaeve C, Schagen SB (2013) Late effects of adjuvant chemotherapy for adult onset non-CNS cancer; cognitive impairment, brain structure and risk of dementia. *Crit Rev Oncol Hematol* 88(1):87-101 Exhibit 19 (provided concurrently by US mail).

Koppelmans V, et al. (2012) Global and focal white matter integrity in breast cancer survivors 20 years after adjuvant chemotherapy. *Hum Brain Mapp* 35(3):889-899 Exhibit 20 (provided concurrently by US mail).

Lee, et al., Induction of Neuronal Vascular Endothelial Growth Factor Expression by cAMP in the Dentate Gyrus of the Hippocampus Is Required for Antidepressant-Like Behaviors. *The Journal of Neuroscience*, 2009. 29(26):8493-8505 Exhibit 21 (provided concurrently by US mail).

Livak & Schmittgen, Analysis of relative gene expression data using real-time quantitative PCR and the 2(-Delta Delta C(T)) Method. *Methods*. Dec. 2001;25(4):402-8 Exhibit 22 (provided concurrently by US mail).

Lunn, et al., (2009) Vascular endothelial growth factor prevents G93A-SOD1-induced motor neuron degeneration. *Developmental neurobiology*, 69, 871-884 Exhibit 23 (provided concurrently by US mail).

Lyons L, ElBeltagy M, Bennett G, Wigmore P (2012) Fluoxetine counteracts the cognitive and cellular effects of 5-fluorouracil in the rat hippocampus by a mechanism of prevention rather than recovery. *PLoS One* 7(1):e30010 Exhibit 24 (provided concurrently by US mail).

Moran, (2012) Cotinine: Beyond that Expected, More than a Biomarker of Tobacco Consumption. *Frontiers in pharmacology*, 3, 173 Exhibit 25 (provided concurrently by US mail).

Raison, et al., Cytokines sing the blues: inflammation and the pathogenesis of depression. *Trends Immunol*. Jan. 2006;27(1):24-31 Exhibit 26 (provided concurrently by US mail).

Rehani K, et al. (2008) Cotinine-induced convergence of the cholinergic and PI3 kinase-dependent anti-inflammatory pathways in innate immune cells. *Biochim Biophys Acta* 1783(3):375-382 Exhibit 27 (provided concurrently by US mail).

Sun, et al., (2006) Vascular endothelial growth factor-B (VEGFB) stimulates neurogenesis: evidence from knockout mice and growth factor administration. *Developmental biology*, 289, 329-335 Exhibit 28 (provided concurrently by US mail).

Tian, et al., A study of the functional significance of epidermal growth factor in major depressive disorder. *Psychiatr Genet*. 2012 .22(4):161-7 Exhibit 29 (provided concurrently by US mail).

Yang, ErbB2 Overexpression Correlates with Increased Expression of Vascular Endothelial Growth Factors A, C, and D in Human Breast Carcinoma. *American Cancer Society*, 2002. 94 (11):2855-61 Exhibit 30 (provided concurrently by US mail); and.

Zhou, et al., Neuronal nitric oxide synthase contributes to chronic stress-induced depression by suppressing hippocampal neurogenesis. *Journal of Neurochemistry*. 2007. 103(5):1843-1854 Exhibit 31 (provided concurrently by US mail).

International Search Report dated Jan. 8, 2016 in connection with the International Application No. PCT/US2015/058625 Exhibit 3 (provided concurrent/y by US mail), dated Nov. 2, 2015.

Moran, (2012) Cotinine: Beynnd that Expected, More than a Biomarker of Tobacco Consumption. *Frontiers in pharmacology*, 3, 173 Exhibit 25 (provided concurrently by US mail).

\* cited by examiner

Figure 9A-D
Fig. 9A
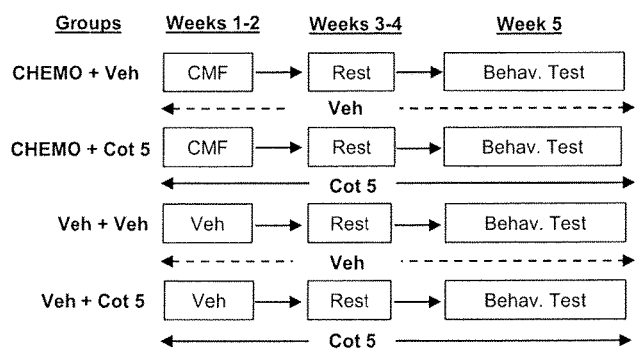
Fig. 9B
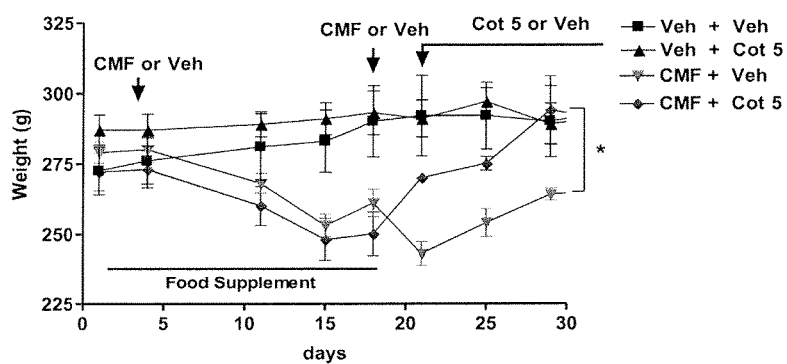
Fig. 9 C
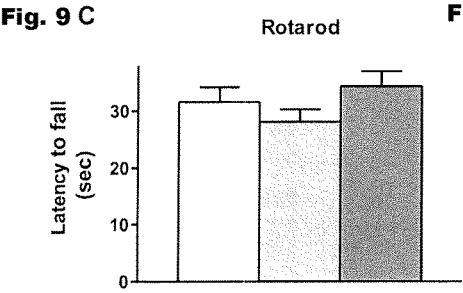
Fig. 9 D
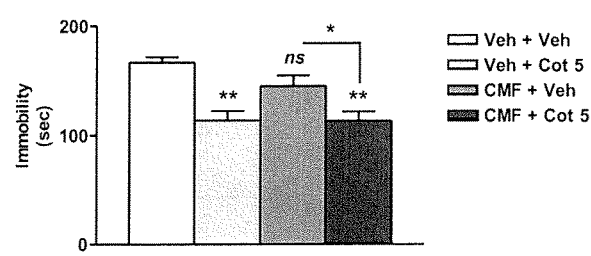

Figure 10A-B
Fig. 10A Familiarization
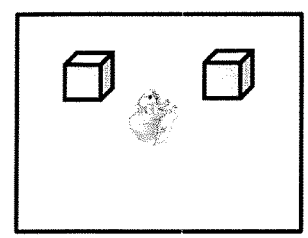
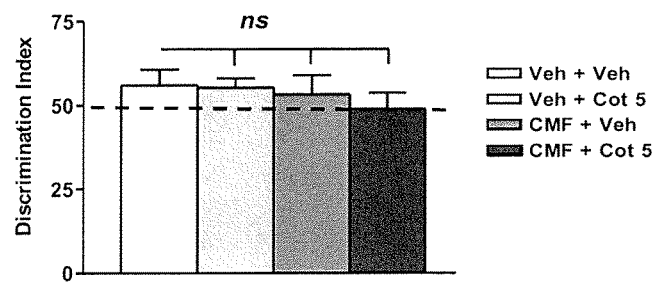
Fig. 10B Novel Location Recognition
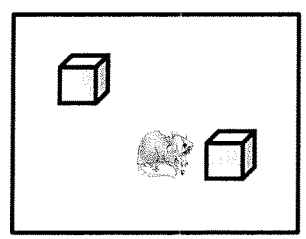
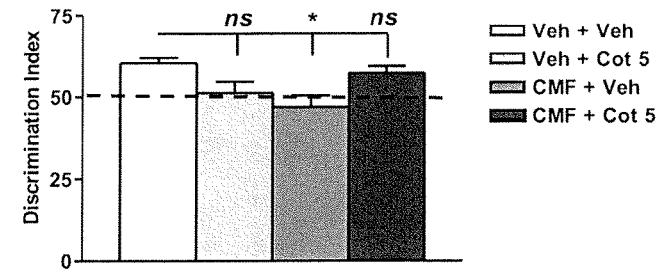

USE OF COTININE IN TREATING OR PREVENTING NEUROGENESIS DEFICITS AND ENHANCING NEUROGENESIS

This application is an 111a application of PCT/US2015/058625, filed Nov. 2, 2015, which claims the benefit of U.S. Provisional Application No. 62/073,339, filed on Oct. 31, 2014, the contents of all of which are incorporated herein by reference in their entireties into the present application.

This invention was made with government support by the United States Department of Veterans Affairs. The government has certain rights in the invention.

Throughout this application various publications are referenced. The disclosures of these publications in their entireties are hereby incorporated by reference into this application in order to more fully describe the state of the art to which this invention pertains.

FIELD OF THE INVENTION

This invention relates to treatment of chemotherapy or stress-related side effects. More specifically, the present invention provides therapeutic methods and compositions for treating chemotherapy treatment or reducing stress-related neuro-inflammation.

BACKGROUND OF THE INVENTION

Cancer is a group of diseases characterized by uncontrolled growth and dissemination of abnormal cells. It was estimated that in 2008 there were 12.7 million new cancer cases worldwide (Belcher E C-GK, Desantis C, Edwards B, Ferlay J, Forman D, Grey N, Harford J, Kramer J, McMikel A, McNeal B, O'Brien M, Pace L, Parkin M, Robbins A, Sankaranarayanan R, Sitas F, Slona R, Sullivan K, Wagner D, Ward E (2011) Global cancer facts and Figures, 2nd edn. American Cancer Society, Atlanta). For many patients afflicted with malignancies, chemotherapy offers the best options for disease control. Though chemotherapy is an effective way to treat many types of cancer, it also carries negative side effects. Patients treated with chemotherapy are at an increased risk of altered brain structure and function (de Ruiter M B, Reneman L, Boogerd W, Veltman D J, van Dam F S, Nederveen A J, Boven E, Schagen S B (2011) Cerebral hyporesponsiveness and cognitive impairment 10 years after chemotherapy for breast cancer. Hum Brain Mapp 32(8):1206-1219). Neurological abnormalities after chemotherapy might result from chemical neurotoxicity, indirect oxidative damage, inflammation or a type of autoimmune response. Clinical studies indicated that up to 70% of cancer patients who received chemotherapy experience cognitive impairment and other symptoms such as fatigue, anxiety and depression. This impairment, commonly named "chemobrain," can affect working memory, attention, processing speed, concentration and executive functions (Christie L A, Acharya M M, Parihar V K, Nguyen A, Martirosian V, Limoli C L (2012) Impaired cognitive function and hippocampal neurogenesis following cancer chemotherapy. Clin Cancer Res 18(7):1954-1965).

For most cancers, survival rates have improved over time, increasing the number of cancer survivors developing these cognitive symptoms (Myers J S (2009) Chemotherapy-related cognitive impairment. Clin J Oncol Nurs 13(4):413-421).

These side effects negatively impact their quality of life, impairing home, educational and occupational activities and unnecessarily extend disease-related disabilities (Harrington C B, Hansen J A, Moskowitz M, Todd B L, Feuerstein M (2010) It's not over when it's over: long-term symptoms in cancer survivors—a systematic review. Int J Psychiatry Med 40(2):163-181). In addition to cognitive deterioration, people treated with chemotherapy may have higher risk of developing depression due to physical suffering or as a complication of therapy itself. For example, long-term prophylaxis with tamoxifen, a selective estrogen receptor modulator commonly used for the hormone receptor-positive breast cancer, has been associated with a higher risk of developing depressive symptoms and cognitive dysfunction (Seliktar N, Polek C, Brooks A, Hardie T (2015) Cognition in breast cancer survivors: hormones versus depression. Psychooncology 24(4):402-407). Currently, there are no completely safe and effective treatments against these side effects (Joly F, Rigal O, Noal S, Giffard B (2011) Cognitive dysfunction and cancer: which consequences in terms of disease management? Psychooncology 20(12):1251-1258). Most memory enhancers currently available have significant side effects or limited efficacy in cancer patients. For example, donepezil, a pro-cholinergic drug, has been studied at the preclinical level, but the attempts to show efficacy in humans have been unsuccessful (Fardell J E, Vardy J, Johnston I N, Winocur G (2011) Chemotherapy and cognitive impairment: treatment options. Clin Pharmacol Ther 90(3):366-376).

One of the main concerns when selecting an antidepressant is the potential effect that the drug can have on the effectiveness or toxicity of the chemotherapeutic regime. For example, treatment of depression in a patient treated with tamoxifen can be complicated by drug interactions. Tamoxifen is a mainly inactive pro-drug, necessitating metabolism by the cytochrome P450 (CYP) pathway, into its active metabolites, 4-hydroxytamoxifen and endoxifen, to achieve its therapeutic effect. Some antidepressants such as the selective serotonin reuptake inhibitors (SSRI) paroxetine and fluoxetine affect the chemotherapy effectiveness by inhibiting the CYPD6 enzyme which metabolizes tamoxifen to its more active metabolites (Brauch H, Mürdter T E, Eichelbaum M, Schwab M (2009) Pharmacogenomics of tamoxifen therapy. Clin Chem 55(10):1770-1782).

Brain magnetic resonance imaging (MRI) analysis in patients treated with high-dose chemotherapy showed white matter lesions that correlated with greater neurocognitive decline (Fouladi M, Chintagumpala M, Laningham F H, Ashley D, Kellie S J, Langston J W, McCluggage C W, Woo S, Kocak M, Krull K, Kun L E, Mulhern R K, Gajjar A (2004) White matter lesions detected by magnetic resonance imaging after radiotherapy and high-dose chemotherapy in children with medulloblastoma or primitive neuroectodermal tumor. J Clin Oncol 22(22):4551-4560). Brain biopsies have shown signs of neurodegeneration and neuroinflammation induced by chemotherapeutic agents such as fragmented axonal fiber and minimally deprived myelination with many scattered macrophages (Choi S M, Lee S H, Yang Y S, Kim B C, Kim M K, Cho K H (2001) 5-fluorouracil-induced leukoencephalopathy in patients with breast cancer. J Korean Med Sci 16(3):328-334). A recent cross-sectional clinical study investigated the effects of adjuvant chemotherapy for breast cancer on the microstructure of cerebral white matter with magnetic resonance imaging (MM) (Koppelmans V, de Groot M, de Ruiter M B, Boogerd W, Seynaeve C, Vernooij M W, Niessen W J, Schagen S B, Breteler M M (2014) Global and focal white matter integrity in breast cancer survivors 20 years after adjuvant chemotherapy. Hum Brain Mapp 35(3):889-899). The study found that among chemotherapy-exposed breast cancer survivors there was a fast deterioration of white matter microstructural integrity (Koppelmans V, de Groot M, de Ruiter M B, Boogerd W, Seynaeve C, Vernooij M W, Niessen W J, Schagen S B, Breteler M M (2014) Global and focal white matter integrity in breast cancer survivors 20 years after adjuvant chemotherapy. Hum Brain Mapp 35(3):889-899). Even though the molecular mechanism(s) and effective therapeutic targets against brain injury induced by chemotherapy are largely unknown, this evidence suggests that chemotherapy induces brain injury and neuroinflammation and may cause the cognitive deficits and mood changes observed in cancer survivors.

However, to date there is no therapeutic agent to diminish cognitive impairment, anxiety, and depression after chemotherapy and long-term side effects associated with chemotherapy. Accordingly, there is not only a need in the art for therapeutic methodologies for increasing or enhancing neurogenesis in neurogenesis deficient individuals, including stress-induced neurogenesis deficits, increasing neurogenesis gene expression, and increasing neuronal cell formation, but also in the case of cancer patients undergoing systemic adjuvant chemotherapy, there is a need to treat the neuropsychological side effects of chemotherapy, such as cognitive impairment and depressive-like behavior induced by chemotherapy. Further, to date there are no methods in place to ameliorate neurogenesis deficits. Accordingly, there is a need in the art for therapeutic methodologies for increasing or enhancing neurogenesis in neurogenesis deficient individuals, including stress-induced neurogenesis deficits, increasing neurogenesis gene expression, and increasing neuronal cell formation.

SUMMARY OF THE INVENTION

The present invention provides a method for treating stress-related neurogenesis deficiency comprising administering a therapeutically effective amount of (5S)-1-methyl-5-(3-pyridyl) pyrrolidin-2-one (cotinine), galantamine, or anatabine to a patient experiencing stress-related neurogenesis deficiency. The present invention also provides a method for inducing neurogenesis gene expression, comprising contacting cell with a therapeutically effective amount of (5S)-1-methyl-5-(3-pyridyl) pyrrolidin-2-one (cotinine), galantamine, or anatabine, where the cell is exposed to stress-related neurogenesis deficiency; wherein the neurogenesis gene is Vegfa, Errb2, Egf, Gdnf, Artn, or a combination thereof. The present invention also provides a method for inhibiting or treating chemotherapy-induced cognitive dysfunction comprising administering a therapeutically effective amount of cotinine to a cancer patient experiencing chemotherapy-induced cognitive dysfunction. The present invention also provides a method for inhibiting or treating chemotherapy-induced memory loss or depression comprising administering a therapeutically effective amount of cotinine to a cancer patient experiencing chemotherapy-induced memory loss or depression. The present invention also provides a method for preventing chemotherapy-induced memory loss or depression comprising administering a therapeutically effective amount of cotinine to a cancer patient prior to chemotherapy or prior to onset of chemotherapy-induced memory loss or depression. The present invention additionally provides a method for treating chemotherapy-induced weight loss comprising administering a therapeutically effective amount of cotinine to a cancer patient experiencing chemotherapy-induced weight loss. The present invention additionally provides a method for treating chemotherapy-induced memory loss, depression and weight loss comprising administering a therapeutically effective amount of cotinine to a cancer patient experiencing chemotherapy-induced memory loss, depression and weight loss.

To define whether cotinine activity correlated with changes in neuroinflammation and neurogenesis in the brain, forced swimming stress was used to induce depressive-like behavior and investigate the effect of cotinine on changes in the expression of genes involved in neuroinflammation or neurogenesis, in the hippocampus. Analysis showed that administering a therapeutically effective amount of (5S)-1-methyl-5-(3-pyridyl) pyrrolidin-2-one to a patient experiencing stress-related neurogenesis deficiency improves neurogenesis despite the stress conditions. Useful doses of (5S)-1-methyl-5-(3-pyridyl) pyrrolidin-2-one are between about 0.1 mg/kg to about 10 mg/kg, such as 0.1 mg/kg, 0.2 mg/kg, 0.3 mg/kg, 0.4 mg/kg, 0.5 mg/kg, 0.75 mg/kg, 0.9 mg/kg, 1.0 mg/kg, 1.0 mg/kg, 1.1 mg/kg, 1.2 mg/kg, 1.25 mg/kg, 1.4 mg/kg, 1.5 mg/kg, 1.75 mg/kg, 1.8 mg/kg, 1.9 mg/kg, 2.0 mg/kg, 2.25 mg/kg, 2.5 mg/kg, 2.75 mg/kg, 3.0 mg/kg, 3.25 mg/kg, 3.5 mg/kg, 3.75 mg/kg, 4.0 mg/kg, 4.25 mg/kg, 4.5 mg/kg, 4.75 mg/kg, 5.0 mg/kg, 5.25 mg/kg, 5.25 mg/kg, 5.5 mg/kg, 5.75 mg/kg, 6.0 mg/kg, 6.25 mg/kg, 6.5 mg/kg, 6.75 mg/kg, 7.0 mg/kg, 7.25 mg/kg, 7.5 mg/kg, 7.75 mg/kg, 8.0 mg/kg, 8.25 mg/kg, 8.5 mg/kg, 8.75 mg/kg, 9.0 mg/kg, 9.25 mg/kg, 9.5 mg/kg, 9.75 mg/kg, or 10.0 mg/kg. Specific doses include about 5 mg/kg or exactly 5 mg/kg.

Alternatively, galantamine can be administered in place of (5S)-1-methyl-5-(3-pyridyl) pyrrolidin-2-one. Dosages of galantamine are optionally about 16 mg/kg/day to about 24 mg/kg/day, and low micromolar concentrations, of 0.1 µM to 1 µM have been tested. Useful dosages are 16 mg/kg/day, 17 mg/kg/day, 18 mg/kg/day, 19 mg/kg/day, 20 mg/kg/day, 21 mg/kg/day, 2 mg/kg/day, 23 mg/kg/day, or 24 mg/kg/day. Similarly, anatabine can be administered in place of (5S)-1-methyl-5-(3-pyridyl) pyrrolidin-2-one. Dosages of anatabine are from about 0.18 mg/kg/day to about 30 mg/kg/day. Useful examples include 0.18 mg/kg/day, 1.6 mg/kg/day, 3.2 mg/kg/day, 5 mg/kg/day, 7.5 mg/kg/day, 10 mg/kg/day, 12.5 mg/kg/day, 15 mg/kg/day, 17.5 mg/kg/day, and 20 mg/kg/day.

The therapeutically effective amount of (5S)-1-methyl-5-(3-pyridyl)pyrrolidin-2-one is optionally administered intramuscularly, intraperitoneally or orally. The composition can be administered daily for up to 2 months after diagnosis of stress-related neuroinflammation, such as from day 1 through day 53 after diagnosis of stress-related neuroinflammation. Alternatively, the composition can be administered starting 7 days before an anticipated stress event.

In some variations, the composition of (5S)-1-methyl-5-(3-pyridyl) pyrrolidin-2-one is administered with a ligand of nicotinic receptor subtype α7 or α4β2. The nicotinic receptor ligand and (5S)-1-methyl-5-(3-pyridyl) pyrrolidin-2-one can be administered concurrently or individually. Where the two compositions, i.e. the nicotinic receptor ligand and (5S)-1-methyl-5-(3-pyridyl) pyrrolidin-2-one are administered individually, there can be a brief time lapse between the two dosings, such as 1 minute, 5 minutes, 10 minutes, 10 minutes, 15 minutes, 20 minutes, 30 minutes, 45 minutes, or 1 hour. The nicotinic receptor ligand is optionally cytisine, epibatidine, varenicline, acetylcholine, nifene, or nicotine. Alternatively, an acetylcholinesterase inhibitor can be administered with the composition of (5S)-1-methyl-5-(3-pyridyl) pyrrolidin-2-one. As with the ligand, the acetylcholinesterase inhibitor can be administered concurrently with (5S)-1-methyl-5-(3-pyridyl) pyrrolidin-2-one or administered individually, with a time lase as described above. In some variations, the acetylcholinesterase inhibitor is administered at about 1 mg/kg to about 23 mg/kg, once per day. A nonlimiting example of an acetylcholinesterase inhibitor is Aricept™ (donepezil hydrochloride, Pfizer Inc., NY, N.Y.).

A composition of (5S)-1-methyl-5-(3-pyridyl) pyrrolidin-2-one is alternatively used to inducing neurogenesis gene expression in a cell is exposed to stress-related neurogenesis deficiency by contacting the cell with a therapeutically effective amount of the composition. Examples of the nueorgenesis genes that are induced include the neurogenesis gene is VEGFa, Errb2, EGF, Gdnf, Artn, or a combination thereof. Genetic analysis allows for the measurement of the relative number of RNA transcripts that an organism is producing at any given time (Kadakkuzha & Puthanveettil, Genomics and proteomics in solving brain complexity. Mol Biosyst. April24. Epub ahead of print). RNA transcripts are produced from the chromosomal genes in order to produce proteins through transcription and translation, respectively (Kadakkuzha & Puthanveettil, Genomics and proteomics in solving brain complexity. Mol Biosyst. April 24.Epub ahead of print). Once mRNA is made it is translated into proteins that the organism uses to respond to the environmental changes (Kadakkuzha & Puthanveettil, Genomics and proteomics in solving brain complexity. Mol Biosyst. April 24.Epub ahead of print).

Gene expression PCR arrays allow for the measurement of a set of mRNA transcripts in an organism at a given time using real time polymerase chain reaction (RT-PCR) (Kadakkuzha & Puthanveettil, Genomics and proteomics in solving brain complexity. Mol Biosyst. April 24. Epub ahead of print).

In some variations, the therapeutically effective amount of (5S)-1-methyl-5-(3-pyridyl) pyrrolidin-2-one is optionally used at a dosage, as described above, or at a concentration of 4 µM to 30 µM. For example, (5S)-1-methyl-5-(3-pyridyl) pyrrolidin-2-one can be used at 4 µM, 5 µM, 6 µM, 7 µM, 8 µM, 9 µM, 10 µM, 11 µM, 12 µM, 14 µM, 15 µM, 16 µM, 17 µM, 18 µM, 20 µM, 22 µM, 24 µM, 25 µM, 26 µM, 28 µM, or 30 µM. Similarly, the composition of (5S)-1-methyl-5-(3-pyridyl) pyrrolidin-2-one is optionally contacted or administered with a nicotinic receptor ligand or acetylcholinesterase inhibitor, as described above.

Testing was designed to analyze the gene expression patterns of mice subjected to stress for both neurogenesis and inflammation and identify a pathway through which cotinine may act. The results show that cotinine reduced the expression of several neuroinflammatory factors including chemokines, cytokines and other factors including Nos2, C3, Ccl3 and Ccr2. Cotinine also decreased the negative effects of stress on the expression of various neurogenesis genes including Artn, Erbb2, EGF, Gdnf and Vegfa. This evidence suggests that cotinine has multiple beneficial effects underlying its pro-cognitives and antidepressant effects. Several neuroinflammatory and neurotrophic factors whose expression is modified by cotinine in forced swimming mice were identified, further elucidating mechanisms by which inflammation causes decreased neurogenesis and the connection between increased inflammation, decreased neurogenesis and depression.

BRIEF DESCRIPTION OF THE DRAWINGS

FIGS. 9A-D provide in vivo mice data showing cotinine stimulated weight regain and reduced depressive like behavior in rats subjected to chemotherapy.

FIGS. 10A-B provide in vivo mice data showing familiarization and novel location recognition with and without administration of cotinine.

DETAILED DESCRIPTION OF THE INVENTION

Definitions

Figure 1:
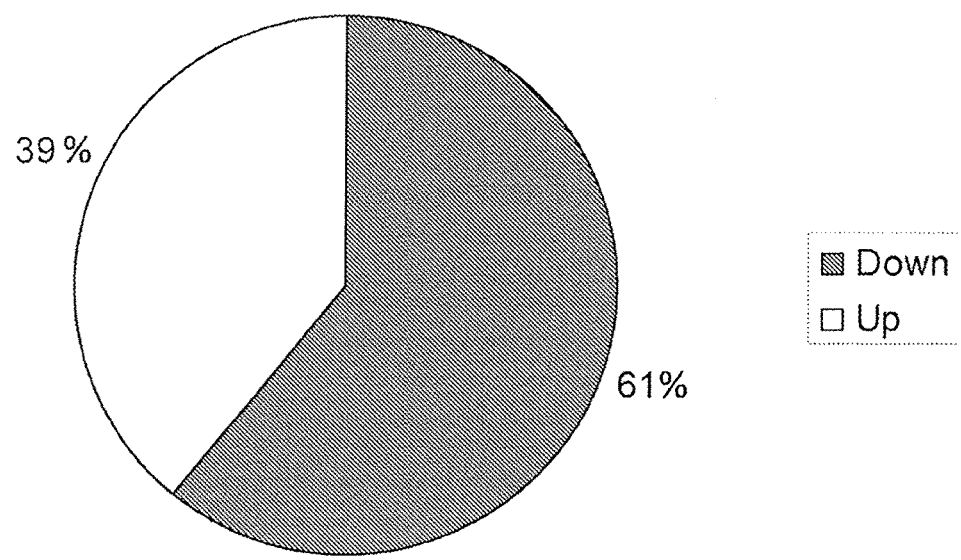
FIG. 1 is a graph showing a summary of the inflammation and autoimmunity genes affected by cotinine treatment.

Unless defined otherwise, all technical and scientific terms used herein have the same meaning as commonly understood by one of ordinary skill in the art to which the present disclosure belongs. As used herein the following terms have the following meanings.

It is to be understood that the present disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

The detailed description of the present disclosure is divided into various sections only for the reader's convenience and disclosure found in any section may be combined with that in another section. Unless defined otherwise, all technical and scientific terms used herein have the same meaning as commonly understood by one of ordinary skill in the art to which the present disclosure belongs.

It must be noted that as used herein and in the appended claims, the singular forms "a", "an", and "the" include plural referents unless the context clearly dictates otherwise. Thus, for example, reference to "a compound" includes a plurality of compounds.

As used herein, the term "about" when used before a numerical designation, e.g., temperature, time, amount, concentration, and such other, including a range, indicates approximations which may vary by (+) or (−) 10%, 5% or 1%.

As used herein "animal" means a multicellular, eukaryotic organism classified in the kingdom Animalia or Metazoa. The term includes, but is not limited to, mammals. Non-limiting examples include rodents, aquatic mammals, domestic animals such as dogs and cats, farm animals such as sheep, pigs, cows and horses, and humans. Wherein the terms "animal" or "mammal" or their plurals are used, it is contemplated that it also applies to any animals.

As used herein the term "patient" is understood to include an animal, especially a mammal, and more especially a human that is receiving or intended to receive treatment.

An "effective amount" refers to an amount effective, at dosages and for periods of time necessary, to achieve the desired therapeutic or prophylactic result.

A "therapeutically effective amount" of a substance/molecule of the invention, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the compositions of the invention are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount. For example, the term "therapeutically effective amount" refers to that amount of a therapy sufficient to result in the amelioration of at least one stress-related neurogenesis deficiency, enhancement of neurogenesis, or induction of one or more neurogenesis genes.

As used herein, enhancement of neurogenesis means a statistically-significant increase in neuronal cell formation, and induction means a statistically-significant increase in neurogenesis gene expression.

As used herein, the term "administration," "administer," or "administering" may be effected in one dose, continuously or intermittently or by several subdoses which in the aggregate provide for a single dose. Dosing can be conducted throughout the course of treatment. Methods of determining the most effective means and dosage of administration are known to those of skill in the art and will vary with the composition used for therapy, the purpose of the therapy, the target cell being treated and the subject being treated. Single or multiple administrations can be carried out with the dose level and pattern being selected by the treating physician. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated and target cell or tissue. Non-limiting examples of route of administration include intratumoral delivery, peritumoral delivery, intraperitoneal delivery, intrathecal delivery, intramuscular injection, subcutaneous injection, intravenous delivery, nasal spray and other mucosal delivery (e.g. transmucosal delivery), intra-arterial delivery, intraventricular delivery, intrasternal delivery, intracranial delivery, intradermal injection, transtympanic injection, electroincorporation (e.g., with electroporation), ultrasound, jet injector, oral, transtympanic, intracochlear and topical patches.

As used herein, "pharmaceutically acceptable carrier" includes any material which, when combined with the reactive agent, retains the reactive agent's biological activity. Examples include, but are not limited to, any of the standard pharmaceutical carriers such as a phosphate buffered saline solution, water, emulsions such as oil/water emulsion, and various types of wetting agents. Other carriers may also include sterile solutions, tablets, including coated tablets and capsules. Typically, such carriers contain excipients, such as starch, milk, sugar, certain types of clay, gelatin, stearic acid or salts, thereof, magnesium or calcium stearate, talc, vegetable fats or oils, gums, glycols, or other known excipients. Such carriers may also include flavor and color additives or other ingredients. Compositions comprising such carriers are formulated by well-known conventional methods.

A "therapeutic agent," as used herein, may be a molecule, or compound that is useful in treatment of a disease or condition. A "therapeutically effective amount," "therapeutically effective concentration" or "therapeutically effective dose" is the amount of a compound that produces a desired therapeutic effect in a subject, such as preventing, inhibiting and/or treating a target condition, alleviating symptoms associated with the condition, producing a desired physiological effect, or allowing imaging or diagnosis of a condition that leads to treatment of the disease or condition. The precise therapeutically effective amount is the amount of the composition that will yield the most effective results in terms of efficacy of treatment in a given subject. This amount will vary depending upon a variety of factors, including, but not limited to, the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of a compound and adjusting the dosage accordingly. For additional guidance, see Remington: The Science and Practice of Pharmacy $21^{(st)}$ Edition, Univ. of Sciences in Philadelphia (USIP), Lippincott Williams & Wilkins, Philadelphia, Pa., 2005.

"Chemotherapy-induced depression" is depression associated with the use of chemotherapeutic agents.

"Chemotherapy-induced memory loss" is memory loss associated with the use of chemotherapeutic agents.

"Chemotherapy-induced weight loss" is weight loss associated the use of one or more chemotherapeutic agents. Normal weight of the subject or patient is defined as the mean weight determined for a 14 day period prior to the use of one or more chemotherapeutic agents. A cancer subject or cancer patient is said to have "chemotherapy-induced weight loss" when following administration of chemotherapeutic agent(s), the weight of the subject or patient decreases more than 5% of normal weight prior to chemotherapy. Merely by way of example, weight loss can be ≥5% weight loss in 30 days, ≥7.5% weight loss in 90 days and/or 10% weight loss in 180 days. Weight loss may be between 5-10% with more serious weight loss exceeding greater than 10%, such as between 10-25%, or greater than 25%. Within the context of this invention, cotinine is not considered a chemotherapeutic agent, but rather cotinine is considered a modulator of body mass (weight) in cancer subjects or cancer patients experiencing "chemotherapy-induced weight loss" or at risk of "chemotherapy-induced weight loss."

"Treating" or "treatment" of a condition, disease or disorder may refer to preventing the condition, disease or disorder, slowing the onset or rate of development of the condition, disease or disorder, reducing the risk of developing the condition, disease or disorder, preventing or delaying the development of symptoms associated with the condition, disease or disorder, reducing or ending symptoms associated with the condition, disease or disorder, generating a complete or partial regression of the condition, disease or disorder, or some combination thereof.

A "subject" is a vertebrate, preferably a mammal, more preferably a human. Mammals include, but are not limited to, farm animals (such as cows), pets (such as cats, dogs and horses), primates, mice and rats.

"Chemotherapy-induced cognitive dysfunction" includes memory loss or decline, thinking/reasoning abilities loss or decline and/or depression."

"Cotinine" includes a composition comprising cotinine, or an isomer or racemate thereof, or a pharmaceutically acceptable salt thereof.

The compositions of the invention can be administered by any parenteral route, e.g., as ear drops, ear wash, ear cream, ear foam, ear ointment, in the form of a pharmaceutical formulation comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

In human therapy, compositions of the invention may be administered alone but may generally be administered in admixture with a suitable pharmaceutical excipient diluent or carrier selected with regard to the intended route of administration and standard pharmaceutical practice.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials. Extemporaneous injection solutions and suspensions may be prepared from sterile powders, granules and tablets of the kind previously described.

METHODS OF THE INVENTION

The present invention provides, for the first time, methods of treating, inhibiting and/or preventing chemotherapy-induced cognitive dysfunction, stress-related neurogenesis deficiency, chemotherapy-induced memory loss or depression; chemotherapy-induced memory loss, depression and weight loss; and/or inducing neurogenesis gene expression.

In an embodiment, "chemotherapy agents or chemotherapeutic agents" refer to methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents.

Merely by way of example, "chemotherapeutic agents" may additionally refer to bifunctional alkylators, such as but not limited to cyclophosphamide, mechlorethamine, chlorambucil, melphalan; monofunctional alkylators, such as but not limited to dacarbazine (DTIC), nitrosoureas, temozolomide (oral dacarbazine), anthracyclines, daunorubicin, doxorubicin, epirubicin, idarubicin, mitoxantrone, valrubicin; cytoskeletal disruptors (taxanes), such as but not limited to taxane, paclitaxel, docetaxel, abraxane, taxotere, epothilones; histone deacetylase inhibitors, such as but not limited to vorinostat, romidepsin; inhibitors of topoisomerase I, such as but not limited to irinotecan, topotecan; inhibitors of topoisomerase II, such as but not limited to etoposide, teniposide, tafluposide; kinase inhibitors, such as but not limited to bortezomib, erlotinib, gefitinib, imatinib, vemurafenib, vismodegib; nucleotide analogs and precursor analogs, such as but not limited to azacitidine, azathioprine, capecitabine, cytarabine, doxifluridine, fluorouracil, gemcitabine, hydroxyurea, mercaptopurine, methotrexate, tioguanine; proteasome inhibitors, such as but not limited to bortezomib; the platinum-based drugs, such as but not limited to cisplatin, oxaliplatin, carboplatin; patients with B-cell non-Hodgkin lymphomas treated with rituximab, cyclophosphamide, doxorubicin, vincristine and prednisone, vincristine and rituximab, or vincristine and bendamustine; and fluorouracil.

The present invention provides a method for treating stress-related neurogenesis deficiency comprising administering a therapeutically effective amount of (5S)-1-methyl-5-(3-pyridyl) pyrrolidin-2-one (cotinine), galantamine, or anatabine to a patient experiencing stress-related neurogenesis deficiency. In one embodiment, the therapeutically effective amount of (5S)-1-methyl-5-(3-pyridyl) pyrrolidin-2-one (cotinine) is about 0.1 mg/kg to about 10 mg/kg. In a further embodiment, the therapeutically effective amount of (5S)-1-methyl-5-(3-pyridyl) pyrrolidin-2-one (cotinine) is about 5 mg/kg, or 5 mg/kg. In another embodiment, the therapeutically effective amount of galantamine is about 16 mg/kg/day to about 24 mg/kg/day, or about 0.1 µM to about 1 µM. In a further embodiment, the therapeutically effective amount of galantamine is 16 mg/kg/day, 17 mg/kg/day, 18 mg/kg/day, 19 mg/kg/day, 20 mg/kg/day, 21 mg/kg/day, 22 mg/kg/day, 23 mg/kg/day, or 24 mg/kg/day. In another embodiment, the therapeutically effective amount of anatabine is about 0.18 mg/kg/day to about 30 mg/kg/day. In a further embodiment, the therapeutically effective amount of anatabine is 0.18 mg/kg/day, 1.6 mg/kg/day, 3.2 mg/kg/day, 5 mg/kg/day, 7.5 mg/kg/day, 10 mg/kg/day, 12.5 mg/kg/day, 15 mg/kg/day, 17.5 mg/kg/day, or 20 mg/kg/day.

In one embodiment, the therapeutically effective amount of (5S)-1-methyl-5-(3-pyridyl) pyrrolidin-2-one (cotinine), galantamine, or anatabine is administered intramuscularly, intraperitoneally or orally. In another embodiment, the cotinine is administered daily for up to 2 months after diagnosis of stress-related neuroinflammation. In a further embodiment, the cotinine is administred daily from day 1 through day 53 after diagnosis of stress-related neuroinflammation. In yet another embodiment the cotinine is administered starting 7 days before an anticipated stress event.

In one embodiment, the method for treating stress-related neurogenesis deficiency further comprises administering a ligand of nicotinic receptor subtype α7 or α4β2, wherein the ligand is cytisine, epibatidine, varenicline, acetylcholine, nifene, or nicotine.

In another embodiment, the method for treating stress-related neurogenesis deficiency further comprises administering an acetylcholinesterase inhibitor. In a further embodiment, the acetylcholinesterase inhibitor is administered at about 1 mg/kg to about 23 mg/kg, once per day.

The present invention provides a method for inducing neurogenesis gene expression, comprising contacting cell with a therapeutically effective amount of (5S)-1-methyl-5-(3-pyridyl) pyrrolidin-2-one (cotinine), galantamine, or anatabine, where the cell is exposed to stress-related neurogenesis deficiency; wherein the neurogenesis gene is Vegfa, Errb2, Egf, Gdnf, Artn, or a combination thereof.

In one embodiment, the therapeutically effective amount of (5S)-1-methyl-5-(3-pyridyl) pyrrolidin-2-one (cotinine) is about 0.1 mg/kg to about 10 mg/kg. In a further embodiment, the therapeutically effective amount of (5S)-1-methyl-5-(3-pyridyl) pyrrolidin-2-one (cotinine) is about 5 mg/kg or 5 mg/kg/day. In another embodiment, the therapeutically effective amount of galantamine is 16 mg/kg/day, 17 mg/kg/day, 18 mg/kg/day, 19 mg/kg/day, 20 mg/kg/day, 21 mg/kg/day, 22 mg/kg/day, 23 mg/kg/day, or 24 mg/kg/day. In a further embodiment, the therapeutically effective amount of galantamine is about 16 mg/kg/day to about 24 mg/kg/day, or about 0.1 µM to about 1 µM. In another embodiment, the therapeutically effective amount of anatabine is about 0.18 mg/kg/day to about 30 mg/kg/day.

The present invention provides a method for inhibiting or treating chemotherapy-induced cognitive dysfunction comprising administering a therapeutically effective amount of cotinine to a cancer patient experiencing chemotherapy-induced cognitive dysfunction.

In one embodiment, the cognitive dysfunction includes loss or impairment of any of attention, executive function, learning and memory, motor function, processing speed, visual-spatial skills, memory and psychomotor function. In one embodiment, the cognitive dysfunction includes memory loss and/or depression. In one embodiment, memory loss is selected from the group consisting of verbal memory, visual memory and working memory and combination thereof.

The present invention provides a method for inhibiting or treating chemotherapy-induced memory loss and/or depression comprising administering a therapeutically effective amount of cotinine to a cancer patient experiencing chemotherapy-induced memory loss or depression.

In one embodiment, cognitive dysfunction is cognitive impairment or loss associated with a chemobrain. In one embodiment, cognitive dysfunction is impairment or loss of brain function following chemotherapy or as a result of administration of chemotherapeutic agent(s) to a cancer subject or cancer patient.

In one embodiment, administration of the therapeutically effective amount of cotinine to the cancer patient additionally inhibits or prevents chemotherapy-induced weight loss or gain. In another embodiment, administration of the therapeutically effective amount of cotinine to the cancer patient additionally restores weight. In a further embodiment, weight is restored at a rate faster than in the absence of cotinine. In a different further embodiment, weight is restored to a greater extent or higher level than in the absence of cotinine.

In one embodiment, the therapeutically effective amount of cotinine is about 0.1 mg/kg to about 10 mg/kg. In another embodiment, the therapeutically effective amount of (5S)-1-methyl-5-(3-pyridyl) pyrrolidin-2-one (cotinine) is about 5 mg/kg or 5 mg/kg. In yet another embodiment, the therapeutically effective amount of (5S)-1-methyl-5-(3-pyridyl) pyrrolidin-2-one (cotinine) is administered intramuscularly, intraperitoneally or orally. In one embodiment, the cotinine is administered daily for up to 2 months after diagnosis of chemotherapy-induced memory loss or depression. In a further embodiment, the cotinine is administered daily from day 1 through day 53 after diagnosis of chemotherapy-induced memory loss or depression.

In one embodiment, the cotinine is administered during a course of chemotherapy. In another embodiment, the cotinine is co-administered with a chemotherapeutic agent. In another embodiment, the cotinine is administered at the same time, before or after administration of a chemotherapeutic agent. In yet another embodiment, the cotinine is administered independent of administration of a chemotherapeutic agent. In one embodiment, the cotinine is administered by the same route as a chemotherapeutic agent. In another embodiment, the cotinine is administered by a different route than the route of administration of a chemotherapeutic agent. In yet another embodiment, the cotinine is administered orally.

In one embodiment, the method for inhibiting or treating chemotherapy-induced memory loss or depression comprising administering a therapeutically effective amount of cotinine to a cancer patient experiencing chemotherapy-induced memory loss or depression additionally comprises administering a positive allosteric modulator of nicotinic receptor subtype α7 or α4β2 or an acetylcholinesterase inhibitor. In a further embodiment, the modulator is cytisine, epibatidine, varenicline, acetylcholine or nifene.

In another embodiment, the method for inhibiting or treating chemotherapy-induced memory loss or depression comprising administering a therapeutically effective amount of cotinine to a cancer patient experiencing chemotherapy-induced memory loss or depression further comprises administering an acetylcholinesterase inhibitor.

In yet another embodiment, where the method for inhibiting or treating chemotherapy-induced memory loss or depression comprising administering a therapeutically effective amount of cotinine to a cancer patient experiencing chemotherapy-induced memory loss or depression additionally comprises administering a positive allosteric modulator of nicotinic receptor subtype α7 or α4β2 or an acetylcholinesterase inhibitor, or where the method for inhibiting or treating chemotherapy-induced memory loss or depression comprising administering a therapeutically effective amount of cotinine to a cancer patient experiencing chemotherapy-induced memory loss or depression further comprises administering an acetylcholinesterase inhibitor, the acetylcholinesterase inhibitor is administered at about 1 mg/kg to about 23 mg/kg, once per day.

In one embodiment, the therapeutically effective amount of cotinine modulates energy balance in a cancer patient afflicted with chemotherapy-induced weight loss. In a further embodiment, weight is restored to a weight prior to administration of a chemotherapeutic agent used to treat cancer in a cancer patient subjected to chemotherapy.

The present invention provides a method for preventing chemotherapy-induced memory loss or depression comprising administering a therapeutically effective amount of cotinine to a cancer patient prior to chemotherapy or prior to onset of chemotherapy-induced memory loss or depression.

In one embodiment, administration of the therapeutically effective amount of cotinine to the cancer patient additionally inhibits or prevents chemotherapy-induced weight loss or gain. In a further embodiment, weight of the cancer patient is at least 95% of body weight prior to chemotherapy. In a different further embodiment, the chemotherapy-induced weight loss is more than 8% of body weight prior to chemotherapy. In another different further embodiment, the chemotherapy-induced weight loss is more than 10% of body weight prior to chemotherapy. In a different further embodiment, the chemotherapy-induced weight loss is more than 15% of body weight prior to chemotherapy. In still another different further embodiment, the chemotherapy-induced weight loss is more than 20% of body weight prior to chemotherapy. In yet another different further embodiment, the chemotherapy-induced weight loss is between 8% to 15% body weight prior to chemotherapy.

In one embodiment, following chemotherapy-induced weight loss, administration of cotinine results in weight regain or weight recovery. In one embodiment, weight regain or weight recovery is faster with administration of cotinine than in its absence. In one embodiment, weight regain or weight recovery is within 95% of (normal) weight prior to chemotherapy. In one embodiment, weight regain or weight recovery is 95-100% of (normal) weight prior to chemotherapy. In one embodiment, weight regain or weight recovery is full weight prior to chemotherapy.

In one embodiment, administration of the therapeutically effective amount of cotinine to the cancer patient additionally maintains weight. In a further embodiment, weight is maintained not less than 95% of weight prior to chemotherapy. In another embodiment, weight is maintained to a level higher with cotinine administration than without cotinine administration in a cancer patient treated with a chemotherapeutic agent for the cancer. In yet another embodiment, the therapeutically effective amount of cotinine is about 0.1 mg/kg to about 10 mg/kg. In another embodiment, the therapeutically effective amount of (5S)-1-methyl-5-(3-pyridyl) pyrrolidin-2-one (cotinine) is about 5 mg/kg or 5 mg/kg. In yet another embodiment, the therapeutically effective amount of (5S)-1-methyl-5-(3-pyridyl) pyrrolidin-2-one (cotinine) is administered intramuscularly, intraperitoneally or orally.

In one embodiment, the cotinine is administered during the course of chemotherapy. In another embodiment, the cotinine is co-administered with a chemotherapeutic agent. In another embodiment, the cotinine is administered at the same time, before or after administration of a chemotherapeutic agent. In yet another embodiment, the cotinine is administered independent of administration of a chemotherapeutic agent. In one embodiment, the cotinine is administered by the same route as a chemotherapeutic agent. In another embodiment, the cotinine is administered by a different route than route of administration of a chemotherapeutic agent. In yet another embodiment, the cotinine is administered orally.

In one embodiment, the method for preventing chemotherapy-induced memory loss or depression comprising administering a therapeutically effective amount of cotinine to a cancer patient prior to chemotherapy or prior to onset of chemotherapy-induced memory loss or depression additionally comprises administering a positive allosteric modulator of nicotinic receptor subtype $\alpha 7$ or $\alpha 4\beta 2$ or an acetylcholinesterase inhibitor. In a further embodiment, the modulator is cytisine, epibatidine, varenicline, acetylcholine or nifene.

In another embodiment, the method for preventing chemotherapy-induced memory loss or depression comprising administering a therapeutically effective amount of cotinine to a cancer patient prior to chemotherapy or prior to onset of chemotherapy-induced memory loss or depression further comprises administering an acetylcholinesterase inhibitor.

In yet another embodiment, where the method for preventing chemotherapy-induced memory loss or depression comprising administering a therapeutically effective amount of cotinine to a cancer patient prior to chemotherapy or prior to onset of chemotherapy-induced memory loss or depression additionally comprises administering a positive allosteric modulator of nicotinic receptor subtype $\alpha 7$ or $\alpha 4\beta 2$ or an acetylcholinesterase inhibitor, or where the method for preventing chemotherapy-induced memory loss or depression comprising administering a therapeutically effective amount of cotinine to a cancer patient prior to chemotherapy or prior to onset of chemotherapy-induced memory loss or depression further comprises administering an acetylcholinesterase inhibitor, the acetylcholinesterase inhibitor is administered at about 1 mg/kg to about 23 mg/kg, once per day.

In one embodiment, where the method of inhibiting or treating chemotherapy-induced memory loss or depression comprising administering a therapeutically effective amount of cotinine to a cancer patient experiencing chemotherapy-induced memory loss or depression, or where the method for preventing chemotherapy-induced memory loss or depression comprising administering a therapeutically effective amount of cotinine to a cancer patient prior to chemotherapy or prior to onset of chemotherapy-induced memory loss or depression, chemotherapy requires administration of one or more chemotherapeutic agent for the cancer. In a further embodiment, the chemotherapeutic agent induces memory loss, depression and/or weight loss in a cancer patient. In a different further embodiment, the chemotherapeutic agent is a systemic chemotherapeutic agent. Suitable examples of the chemotherapeutic agent have been described hereinabove. For example, the chemotherapeutic agents comprise cyclophosphamide, methotrexate or 5-fluorouracil. In yet another different further embodiment, the chemotherapeutic agent includes but is not limited to any of cyclophosphamide, methotrexate and 5-fluorouracil.

The present invention provides a method for treating chemotherapy-induced memory loss, depression and weight loss comprising administering a therapeutically effective amount of cotinine to a cancer patient experiencing chemotherapy-induced memory loss, depression and/or weight loss.

In one embodiment, the chemotherapy does not impair motor function. In another embodiment, the impairment of motor function is long-term. In a further embodiment, long-term is 2 weeks or more following chemotherapy. In one embodiment, administration of the therapeutically effective amount of cotinine to the cancer patient additionally restores weight. In a further embodiment, weight is restored at a rate faster than in the absence of cotinine. In a different further embodiment, weight is restored to a greater extent or higher level than in the absence of cotinine.

In one embodiment, the therapeutically effective amount of cotinine is about 0.1 mg/kg to about 10 mg/kg. In another embodiment, the therapeutically effective amount of (5S)-1-methyl-5-(3-pyridyl) pyrrolidin-2-one (cotinine) is about 5 mg/kg or 5 mg/kg. In yet another embodiment, the therapeutically effective amount of (5S)-1-methyl-5-(3- pyridyl) pyrrolidin-2-one (cotinine) is administered intramuscularly, intraperitoneally or orally.

In one embodiment, the cotinine is administered daily for up to 2 months after diagnosis of chemotherapy-induced memory loss or depression. In a further embodiment, the cotinine is administered daily from day 1 through day 53 after diagnosis of chemotherapy-induced memory loss or depression.

In one embodiment, the cotinine is administered during the course of chemotherapy. In another embodiment, the cotinine is co-administered with a chemotherapeutic agent. In another embodiment, the cotinine is administered at the same time, before or after administration of a chemotherapeutic agent. In yet another embodiment, the cotinine is administered independent of administration of a chemotherapeutic agent. In one embodiment, the cotinine is administered by the same route as a chemotherapeutic agent. In another embodiment, the cotinine is administered by a different route than route of administration of a chemotherapeutic agent. In yet another embodiment, the cotinine is administered orally.

In one embodiment, the method for treating chemotherapy-induced memory loss, depression and weight loss comprising administering a therapeutically effective amount of cotinine to a cancer patient experiencing chemotherapy-induced memory loss, depression and weight loss additionally comprises administering a positive allosteric modulator of nicotinic receptor subtype α7 or α4β2 or an acetylcholinesterase inhibitor. In a further embodiment, the modulator is cytisine, epibatidine, varenicline, acetylcholine or nifene.

In another embodiment, the method for treating chemotherapy-induced memory loss, depression and weight loss comprising administering a therapeutically effective amount of cotinine to a cancer patient experiencing chemotherapy-induced memory loss, depression and weight loss further comprises administering an acetylcholinesterase inhibitor.

In yet another embodiment, where the method for treating chemotherapy-induced memory loss, depression and weight loss comprising administering a therapeutically effective amount of cotinine to a cancer patient experiencing chemotherapy-induced memory loss, depression and weight loss additionally comprises administering a positive allosteric modulator of nicotinic receptor subtype α7 or α4β2 or an acetylcholinesterase inhibitor, or where the method for treating chemotherapy-induced memory loss, depression and weight loss comprising administering a therapeutically effective amount of cotinine to a cancer patient experiencing chemotherapy-induced memory loss, depression and weight loss further comprises administering an acetylcholinesterase inhibitor, the acetylcholinesterase inhibitor is administered at about 1 mg/kg to about 23 mg/kg, once per day.

In one embodiment, the therapeutically effective amount of cotinine modulates energy balance in a cancer patient afflicted with chemotherapy-induced weight loss. In a further embodiment, weight is restored to a weight prior to administration of a chemotherapeutic agent used to treat cancer in a cancer patient subjected to chemotherapy.

In one embodiment, chemotherapy requires administration of one or more chemotherapeutic agent for the cancer. In a further embodiment, the chemotherapeutic agent induces memory loss, depression and/or weight loss in a cancer patient. In a different further embodiment, the chemotherapeutic agent is a systemic chemotherapeutic agent.

In accordance with the practices of the invention, cotinine can be administered free of nicotine.

In another embodiment, memory comprises working memory. In a further embodiment, working memory is spatial recognition memory.

In accordance with the practices of the invention, memory loss can be associated with a decrease in cell proliferation and synaptic density in the hippocampus.

In one embodiment, chemotherapy comprises administration of one or more chemotherapeutic agents. In a further embodiment, administration of one or more chemotherapeutic agents occurs over one or more times.

In accordance with the practices of the invention, cotinine is administered following last dose of a chemotherapeutic agent. In another embodiment, cotinine is administered following first dose of a chemotherapeutic agent but before chemotherapy-induced memory loss, depression or weight loss. In yet another embodiment, cotinine is administered with a chemotherapeutic agent.

Compositions

The invention provides a composition comprising cotinine and/or hydrates of cotinine and/or salts of cotinine for use in the methods of the invention.

In accordance with the practice of the invention, the administration of a given drug may be effected locally or systemically. Additionally, the route of administration of a given drug may be any of topical, enteral or parenteral. In other embodiments of the invention, the route of administration of a given drug may be any of rectal, intercisternal, bucal, intramuscular, intrasternal, intracutaneous, intrasynovial, intravenous, intraperitoneal, intraocular, periostal, intra-articular injection, infusion, oral, inhalation, subcutaneous, implantable pump, continuous infusion, gene therapy, intranasal, intrathecal, intracerebroventricular, transdermal, or by spray, patch or injection.

In accordance with the practice of the invention, the route of administration of a given drug can vary during a course of treatment, or during a given day. For example, if a given drug is administered in conjunction with one or more additional drugs, each additional drug may be administered by identical or different routes compared to the other drugs.

In accordance with the practice of the invention, the drug can be administered one or more times a day, daily, weekly, monthly or yearly.

The present invention provides pharmaceutical formulations (also known as pharmaceutical compositions or dosage forms) comprising a first active agent (e.g., cotinine), one or more additional active agent (e.g., a ligand of nicotinic receptor, a positive allosteric modulator or other active agent), and a pharmaceutically acceptable carrier or vehicle.

Pharmaceutically acceptable carrier or vehicle refers to a non-toxic solid, semisolid (also referred to herein as softgel) or liquid filler, diluent, encapsulating material or formulation auxiliary of any type. The invention also provides methods for treating or ameliorating cotinine modulated diseases using said pharmaceutical formulations.

Dosage Forms

Dosage forms can be made according to well-known methods in the art. Some preferred methods are described below.

The pharmaceutical compositions of the invention may be formulated as solid dosage forms, such as capsules, pills, softgels, tablets, caplets, troches, wafer, sprinkle, chewing gum or the like, for oral administration. The pharmaceutical compositions of the invention may also be formulated as liquid dosage forms such as elixir, suspension or syrup.

The pharmaceutical compositions of the invention may also be presented in a dosage form for transdermal application, for example an ointment for children, a form for oral administration, for example a slow release product, or in gastro-resistant tablet form or gum form. They may also be in spray, bronchial form or eye lotion form, or other galenic forms with programmed mucosal and secondarily per os disintegration.

Therefore the different pharmaceutical compositions of the invention can be administered by several routes chosen in accordance with the patient's pathological profile and age. For children, the patch form, syrup form or tablets to be dissolved in the mouth. The other forms, eye lotion or injection may also be used. In adults all galenic forms (also known as dosage forms) can be contemplated.

The advantage of a coupled or combined galenic form also provides simplicity of treatment, patient compliance with the simplified treatment and therefore a more successful outcome.

The pharmaceutical compositions of the present invention may be mixed with pharmaceutically acceptable carriers, binders, diluents, adjuvants, excipients, or vehicles, such as preserving agents, fillers, polymers, disintegrating agents, glidants, wetting agents, emulsifying agents, suspending agents, sweetening agents, flavoring agents, perfuming agents, lubricating agents, acidifying agents, coloring agent, dyes, preservatives and dispensing agents, or compounds of a similar nature depending on the nature of the mode of administration and dosage forms. Such ingredients, including pharmaceutically acceptable carriers and excipients that may be used to formulate oral dosage forms, are described in the Handbook of Pharmaceutical Excipients, American Pharmaceutical Association (1986), incorporated herein by reference in its entirety.

Pharmaceutically acceptable carriers are generally non-toxic to recipients at the dosages and concentrations employed and are compatible with other ingredients of the formulation. Examples of pharmaceutically acceptable carriers include water, saline, Ringer's solution, dextrose solution, ethanol, polyols, vegetable oils, fats, ethyl oleate, liposomes, waxes polymers, including gel forming and non-gel forming polymers, and suitable mixtures thereof. The carrier may contain minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulin; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG. Preferably the carrier is a parenteral carrier, more preferably a solution that is isotonic with the blood of the recipient.

Examples of binders include, but are not limited to, microcrystalline cellulose and cellulose derivatives, gum tragacanth, glucose solution, acacia mucilage, gelatin solution, molasses, polvinylpyrrolidine, povidone, crospovidones, sucrose and starch paste.

Examples of diluents include, but are not limited to, lactose, sucrose, starch, kaolin, salt, mannitol and dicalcium phosphate.

Examples of excipients include, but are not limited to, starch, surfactants, lipophilic vehicles, hydrophobic vehicles, pregelatinized starch, Avicel, lactose, milk sugar, sodium citrate, calcium carbonate, dicalcium phosphate, and lake blend purple. Typical excipients for dosage forms such as a softgel include gelatin for the capsule and oils such as soy oil, rice bran oil, canola oil, olive oil, corn oil, and other similar oils; glycerol, polyethylene glycol liquids, vitamin E TPGS as a surfactant and absorption enhancer (Softgels: Manufacturing Considerations; Wilkinson P, Foo Sog Hom, Special Drug Delivery Systems; Drugs and the Pharmaceutical Sciences Vol 41 Praveen Tyle Editor, Marcel Dekker 1990, 409-449; Pharmaceutical Dosage Forms and Drug Delivery by Ansel, Popovich and Allen 1995, Williams and Wilkins, Chapter 5 pp 155-225). Tritoqualine and anti H1 may form either a solution in a selected oil vehicle or a suspension of fine particles (comprising any of the excipients disclosed herein, e.g., typical excipients for softgels).

Examples of disintegrating agents include, but are not limited to, complex silicates, croscarmellose sodium, sodium starch glycolate, alginic acid, corn starch, potato starch, bentonite, methylcellulose, agar and carboxymethylcellulose.

Examples of glidants include, but are not limited to, colloidal silicon dioxide, talc, corn starch.

Examples of wetting agents include, but are not limited to, propylene glycol monostearate, sorbitan monooleate, diethylene glycol monolaurate and polyoxyethylene laural ether.

Examples of sweetening agents include, but are not limited to, sucrose, lactose, mannitol and artificial sweetening agents such as saccharin, and any number of spray dried flavors.

Examples of flavoring agents include, but are not limited to, natural flavors extracted from plants such as fruits and synthetic blends of compounds which produce a pleasant sensation, such as, but not limited to peppermint and methyl salicylate.

Examples of lubricants include magnesium or calcium stearate, sodium lauryl sulphate, talc, starch, lycopodium and stearic acid as well as high molecular weight polyethylene glycols.

Examples of coloring agents include, but are not limited to, any of the approved certified water soluble FD and C dyes, mixtures thereof; and water insoluble FD and C dyes suspended on alumina hydrate.

The artisan of ordinary skill in the art will recognize that many different ingredients can be used in formulations according to the present invention, in addition to the active agents, while maintaining effectiveness of the formulations in treating the H4R modulated diseases. The list provided herein is not exhaustive.

Kits

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The kit can contain a pharmaceutical composition that includes one or more agents of the invention effective for treating, inhibiting and/or preventing impairment associated with chemotherapy-induced memory loss or depression. It may further include other materials desirable from a commercial and user standpoint, including other buffers, diluents, filters, needles, syringes, and package inserts with instructions for use.

The agents may be provided as dry powders, usually lyophilized, including excipients that upon dissolving will provide a reagent solution having the appropriate concentration.

The kit comprises one or more containers with a label and/or instructions. The label can provide directions for carrying out the preparation of the agents for example, dissolving of the dry powders, and/or treatment for impairment associated with chemotherapy-induced memory loss or depression.

The label and/or the instructions can indicate directions for in vivo use of the pharmaceutical composition. The label and/or the instructions can indicate that the pharmaceutical composition is used alone, or in combination with another agent to treat an impairment associated with chemotherapy-induced memory loss or depression The label can indicate appropriate dosages for the agents of the invention as described supra.

Suitable containers include, for example, bottles, vials, and test tubes. The containers can be formed from a variety of materials such as glass or plastic. The container can have a sterile access port (for example the container can be an intravenous solution bag or a vial having a stopper pierceable by a needle such as a hypodermic injection needle).

The following example is intended merely to illustrate the practice of the present invention and is not provided by way of limitation. The disclosures of all patent and scientific literatures cited herein are expressly incorporated in their entirety by reference.

Example 1

Two-month-old male C57BU6J mice (The Jackson Laboratory, Bar Harbor, Me.), weighing 25-30 g were maintained on a 12-hours light/dark cycle (light on at 07:00) with ad libitum access to food and water and maintained at a regulated temperature of 25±1"C. Upon arrival mice were group-housed and acclimated for 7 days before any intervention.

Mice were randomly divided into three groups as follows: group 1 controls that were not exposed to stress (NES) and treated with vehicle (phosphate buffered saline, PBS); group 2 controls subjected to forced swimming stress (FSB) and treated with vehicle; group 3 subjected to forced swimming stress and treated with cotinine (FSA).

Cotinine ((5S)-1-methyl-5-(3-pyridyl) pyrrolidin-2-one; Sigma-Aldrich Corporation, St. Louis, Mo., USA) solutions were prepared by dissolving the powdered compound in sterile phosphate buffered saline (PBS), and vehicle (PBS). Mice were treated with vehicle or cotinine (5 mg/kg) via gavage. The gavage technique was performed by well trained personnel and did not induce significant stress in the mice. All investigators were blind to treatment groups and doses were chosen based on previously studies (Zeitlin, et al., (2012) Cotinine enhances the extinction of contextual fear memory and reduces anxiety after fear conditioning. Behav Brain Res, 228, 284-293.). Treatments were administered for 7 days before the induction of stress. For all animals, treatment continued from the onset of treatment until euthanasia.

To induce chronic stress, mice were subjected to repetitive forced swimming (FS) for six consecutive days, for six minutes each day, as described previously (Furukawa-Hibi, et al., (2011) The hydrophobic dipeptide Leu-lie inhibits immobility induced by repeated forced swimming via the induction of BDNF. Behav Brain Res. 2011 Jul. 7; 220(2): 271-280). Each mouse was placed in an inescapable transparent plastic cylinder (40 centimeters (cm) high×20 cm in diameter) filled with water to a depth of 30 cm, for six minutes. Water temperature was maintained at 24-25° C. and water was changed between all trials. In all cases, following exposure, animals were retrieved, dried with a hand towel and returned to their home cages. Mice assigned to NES control group were removed from the animal housing facility and taken to the behavioral testing room during the same period of time than FS mice, but remained in their home cages during the FS period. In all experiments, no mice needed assistance to avoid drowning.

Experiments were performed during the light period of the circadian cycle and in accordance with the National Institutes of Health standards.

Following behavioral experimentation, euthanasia was performed via cervical dislocation under anesthesia with isofluorane (4% induction, 2% maintenance) by investigators not assigned to prior work with the mice blinded to the treatments. Whole brains were collected and immediately stored frozen at −80° C.

The hippocampi were dissected on ice and placed into RNAlater tubes (Life Technologies; Thermo Fisher Scientific, Waltham, Mass.). RNAlater is a proprietary solution which protects RNA in tissue samples from degradation to allow for analysis at a later date. RNase free conditions were created and maintained throughout the procedure by washing labware in a 0.1% DEPC solution followed by rinsing with RNase free water. Total RNA extraction and purification was performed using RNeasy Lipid Tissue Extraction Kit (Qiagen N.V., Venlon NL). Sample homogenization was performed using Kontes Pellet Pestle Cordless Motor and/or 20 gauge needle and syringe. Samples were extracted using a Qiazol/Chloroform extraction. The samples were purified on an RNeasy spin column using multiple washes. An on-column DNase incubation was performed in order to remove contaminating DNA. The entire extraction and purification step was performed twice to remove all contaminating DNA for samples ran on the neurogenesis arrays. Samples were eluted in RNase free water.

Nucleic acid quantification was performed on the RNA, to determine how many microliters of sample to add to the cDNA reaction, as the reaction requires a specific concentration of RNA to achieve optimal results. Nucleic acid quantification was performed using a NanoDrop spectrophotometer (Thermo Fisher Scientific, Waltham, Mass.). The absorbance of each sample was measured by applying 1 µl to the platform. Concentration was calculated using the absorbance values for 260 nm using Beer's Law. The spectra were examined for the presence of a single peak and the 260/280 nm ratio was expected to be near 2.0 for high quality RNA. The quality and quantity of total RNA was determined spectrophotometrically with an Agilent 2100 Bioanalyzer (Agilent Technologies, Palo Alto, Calif.). The samples were selected for RT-PCR experiments provided that they had a >2.0 RNA integrity number.

cDNA was synthesized using $RT^2$ First strand kits (SABiosciences; Qiagen N.V., Venlon NL) to prepare cDNA from purified total RNA. First, a genomic DNA elimination step was performed. Following DNA removal, the RNA preparation was incubated at 42QC for five minutes and placed on ice. First strand synthesis reaction was performed by adding 4 µl of 5× RT Buffer, 1 µl of Primer and External Control mix and 2 µl of RT Enzyme Mix and 3 µl of RNase free water to each sample. The mixture was incubated at 42QC for exactly 15 minutes and then immediately heated to 95QC for 5 minutes using an iCycler thermal cycler (Bio-Rad Laboratories, Inc., Hercules, Calif.). Finally, 91 µI of RNase free water was added to each cDNA synthesis reaction.

The effect of cotinine on neurogenesis and neurogenesis gene induction was analyzed using RT2 Profiler PCR arrays (SABiosciences; Qiagen N.V., Venlon NL) on the hippocampus of mice subjected to forced swimming stress. These arrays consisted of 96 well plates, with pre-dispensed sets of primers and controls, which are designed to target the gene expression of specific pathways using RT-PCR analysis. Each array contains the primers for the analysis of 84 genes in a specific pathway, 3 reverse transcription controls, 1 genomic DNA control and 3 PCR positive controls. Sample cDNA, prepared from mRNA, is loaded onto each plate and then subjected to RT-PCR. RT-PCR creates a copy of the target region of cDNA, resulting in a doubling of template in each cycle (Livak & Schmittgen, Analysis of relative gene expression data using real-time quantitative PCR and the 2(-Delta Delta C(T)) Method. Methods. 2001 Dec.; 25(4): 402-8). SYBR green is used as a labeling agent, which allows the RT-PCR instrument (DNA Engine Opticon) to measure signal levels. SYBR green intercalates between double stranded DNA molecules which are formed during PCR. The relative amount of mRNA expression can be measured because the amount of fluorescence is proportional to amount of template present (Livak & Schmittgen, Analysis of relative gene expression data using real-time quantitative PCR and the 2(-Delta Delta C(T)) Method. Methods. 2001 Dec.; 25(4):402-8). Comparing the relative level of mRNA expression in one condition to the relative level of mRNA expression present in another condition, can indicate how an organism is regulating the levels of proteins produced in response to changes in external stimuli (Livak & Schmittgen, Analysis of relative gene expression data using real-time quantitative PCR and the 2(-Delta Delta C(T)) Method. Methods. 2001 Dec.; 25(4):402-8).

Example 2

To study whether the effect of cotinine was linked to an anti-inflammatory effect, the expression of inflammation genes in the hippocampus of stressed mice was compared in treated (cotinine) versus nontreated (vehicle), using the inflammation and autoimmunity gene expression arrays. Inflammatory response and Autoimmunity PCR arrays (PAMM-077Z) (SABiosciences; Qiagen N.V., Venlon NL) were loaded and placed into a DNA Engine Opticon RT-PCR instrument (Bio-Rad Laboratories, Inc., Hercules, Calif.). A mix of 1,350 µl 2×RT2 SYBR Green Mastermix, 102 µl cDNA synthesis reaction, and 1,248 µl of RNase-free water was prepared for each sample. Using a multichannel pipette, samples obtained as per Example 1 were loaded into each well of the 96-well plates. Thermal cycling was performed as follows: 1 cycle of 95° C. for 10 minutes, followed by 40 cycles of 15 seconds at 95° C., 1 minute at 60° C., and data collection. A melt curve was performed to assay the reaction specificity as follows 95° C. for 1 minute, followed by an incremental increase of 0.5° C. every 2 seconds from 55 to 95° C. and data collection.

PCR array data was then analyzed. Raw data Ct values were determined and exported to an Excel spreadsheet using Opticon Monitor 3 software (Bio-Rad Laboratories, Inc., Hercules, Calif.). Each plate was examined to determine the appropriate baseline and threshold values. The CtPPC for each sample was 20 Ct±0.5 for all arrays. Ct values ≥35 were considered negative. Data analysis was performed using the PCR Array Data Analysis website (SABiosciences; Qiagen N.V., Venlon NL). Data was normalized using multiple housekeeping genes—Hprtl, Gapdh and Actb—as well as other genes on the plate with the smallest changes in raw Ct values. Fold regulation was calculated using the delta delta Ct method (lmpey, et al., Stimulation of cAMP response element (CRE)-mediated transcription during contextual learning. Nat Neurosci. 1998. 1(7):595-601). Delta Ct was calculated using the average Ct value for the gene of interest minus the average Ct value for the selected housekeeping genes (Livak & Schmittgen, Analysis of relative gene expression data using real-time quantitative PCR and the 2(-Delta Delta C(T)) Method. Methods. 2001 Dec.; 25(4):402-8). These values were averaged to obtain the average delta Ct (Livak & Schmittgen, Analysis of relative gene expression data using real-time quantitative PCR and the 2(-Delta Delta C(T)) Method. Methods. 2001 Dec.; 25(4):402-8). Then, delta delta Ct was calculated by subtracting the delta Ct value for the control from the delta ct value from the gene of interest (Livak & Schmittgen, Analysis of relative gene expression data using real-time quantitative PCR and the 2(-Delta Delta C(T)) Method. Methods. 2001 Dec.; 25(4):402-8). Fold change was calculated using 2-Ct for each condition (Livak & Schmittgen, Analysis of relative gene expression data using real-time quantitative PCR and the 2(-Delta Delta C(T)) Method. Methods. 2001 Dec.; 25(4):402-8).

The results showed 61% of the inflammation genes analyzed were down-regulated in the stressed mice treated with cotinine, as seen in FIG. 1. Using a cut off of two-fold difference in regulation, 10 genes were differentially expressed in the stressed mouse treated with cotinine versus the stressed mouse treated with vehicle, seen in Table 1. The following genes were found down-regulated: Complement component 3(C3), Ccl3, Ccr2, Fos and Nos2 and up regulated Ccl1, Ccl2, Ccr4, Tlr1 and Tnfsf14 in the hippocampal extracts.

TABLE 1

The relative change in gene expression induced by cotinine, expressed as fold negative or positive regulation respect to control vehicle-treated mice.

| Gene abbreviation | Gene Name | Fold regulation comparinq to FSB |
|---|---|---|
| C3 | Complement component 3 | −2.89 |
| Ccl1 | Chemokine (C-C motif) liqand 1 | 2.21 |
| Ccl2 | Chemokine (C-C motif) liqand 2 | 2.46 |
| Ccl3 | Chemokine (C-C motif) ligand 3 | −4.00 |
| Ccr2 | Chemokine (C-C motif) receptor 2 | −2.87 |
| Ccr4 | Chemokine (C-C motif) receptor 4 | 2.96 |
| Fos | FBJ osteosarcoma oncoqene | −2.55 |
| Nos2 | Nitric oxide synthase 2, inducible | −3.93 |
| Tlr1 | Toll-like receptor 1 | 2.32 |
| Tnfsf1 | Tumor necrosis factor (ligand) superfamily, member 14 | 6.18 |

FBJ osteosarcoma oncogene (Fos) expression was decreased by 2.5 fold in the brain of the mouse subjected to forced swimming treated with cotinine compared to the mouse subjected to forced swimming and treated with vehicle. Complement component 3 (C3), was decreased by 2.9 fold in the mouse subjected to forced swimming treated with cotinine compared to the stressed mouse treated with vehicle. Five members of the chemokine family were differentially expressed, with some chemokines up regulated by cotinine treatment and stress induction (Ccl1, Ccl2 and Ccr4), while most of the cytokines and chemokines were modestly down regulated by cotinine in the stressed mouse. More dramatic changes were observed in the chemokines Ccl3 (2.8 fold) and Ccr2 (4.0 fold).

Example 3

To study whether administration of cotinine was linked to an enhancement of neurogenesis in the hippocampus, the expression of neurogenesis genes in the brains of vehicle-treated and cotinine-treated mice were compared. Neurogenesis and a neural stem cell real-time polymerase chain reaction (RT-PCR) arrays were used to determine the effect of cotinine on the expression of neurogenesis genes in the hippocampus of mice. The RT-PCR reaction basically consists in quantifying a fluorescent dye that intercalates with the complementary DNA (cDNA) amplified in each cycle. In this array, the RT-PCR reactions allow the simultaneous detection and quantification of the expression of 84 genes coding for stem cell specific biomarkers known to have positive or negative effects on the regulation of cell proliferation, cell differentiation, synaptic function, apoptosis, cell adhesion, and cell signaling of neurogenesis.

PCR array data was then analyzed. Raw data Ct values were determined and exported to an Excel spreadsheet using Opticon Monitor 3 software (Bio-Rad Laboratories, Inc., Hercules, Calif.). Each plate was examined to determine the appropriate baseline and threshold values. The CtPPC for each sample was 20 Ct±0.5 for all arrays. Ct values ≥35 were considered negative. Data analysis was performed using the PCR Array Data Analysis website (SABiosciences; Qiagen N.V., Venlon NL). Data was normalized using multiple housekeeping genes—Hprtl, Gapdh and Actb—as well as other genes on the plate with the smallest changes in raw Ct values. Fold regulation was calculated using the delta delta Ct method (lmpey, et al., Stimulation of cAMP response element (CRE)-mediated transcription during contextual learning. Nat Neurosci. 1998. 1(7):595-601). Delta Ct was calculated using the average Ct value for the gene of interest minus the average Ct value for the selected housekeeping genes (Livak & Schmittgen, Analysis of relative gene expression data using real-time quantitative PCR and the 2(-Delta Delta C(T)) Method. Methods. 2001 Dec.; 25(4):402-8). These values were averaged to obtain the average delta Ct (Livak & Schmittgen, Analysis of relative gene expression data using real-time quantitative PCR and the 2(-Delta Delta C(T)) Method. Methods. 2001 Dec.; 25(4):402-8). Then, delta delta Ct was calculated by subtracting the delta Ct value for the control from the delta ct value from the gene of interest (Livak & Schmittgen, Analysis of relative gene expression data using real-time quantitative PCR and the 2(-Delta Delta C(T)) Method. Methods. 2001 Dec.; 25(4):402-8). Fold change was calculated using 2-Ct for each condition (Livak& Schmittgen, Analysis of relative gene expression data using real-time quantitative PCR and the 2(-Delta Delta C(T)) Method. Methods. 2001 Dec.; 25(4):402-8).

Ten samples were tested using the neurogenesis gene expression arrays: three hippocampal samples from mice that were subjected forced swimming and treated with cotinine (FSA), three hippocampal samples from mice that were subjected forced swimming and treated with vehicle (FSB) and four samples from control mice that were not exposed to stress (NEB) and treated with vehicle.

In the samples from mice th It has been established that biologically significant changes in neural tissue can occur with very small changes in gene expression, not the traditional cut off of two-fold change normally expected in non-brain tissues (Soverchia, et al., Microarrays—The Challenge of Preparing Brain Tissue Samples. Addiction Biology. Mar. 2005 10, 5-13). For the neurogenesis arrays, a criterion of probable significant change that consists of an arbitrary cut-off of 1.3-fold change in gene expression combined an observable opposite effect on expression induced by cotinine was established. For example, in mice subjected to forced swimming, if a gene was negatively expressed in the brain of mice treated with vehicle at −1.3-fold, but was positively expressed in the mice treated with cotinine at 1.2-fold, it was selected. First, to determine if forced swimming was having an impact on gene expression, we compared gene expression levels in mice of each treatment arm subjected to forced swimming to the ones found in mice that were not exposed to stress.

Figure 2:
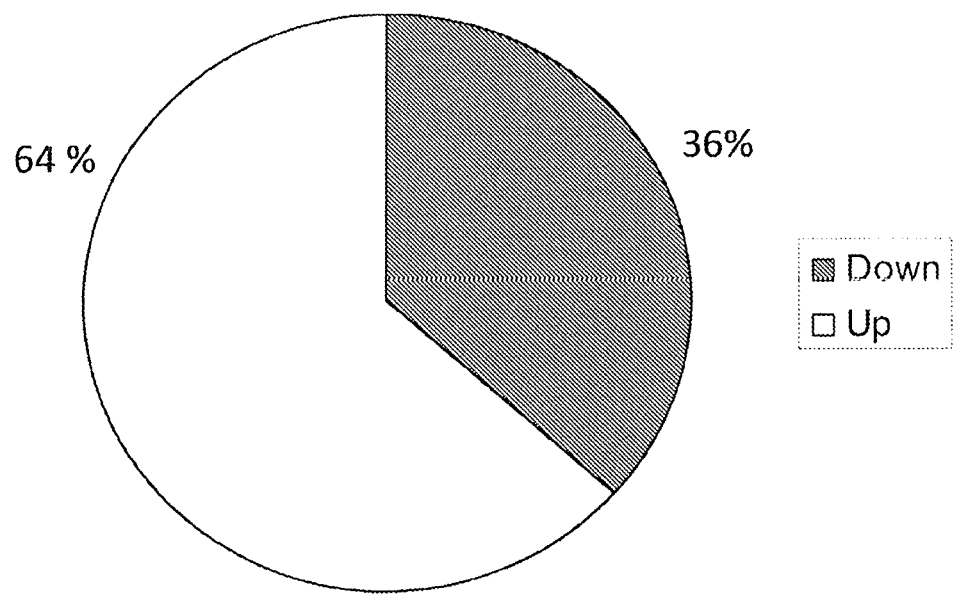
FIG. 2 is a graph showing a summary of the neurogenesis genes affected by cotinine treatment.

In the samples from mice that had been subjected to forced swimming stress and treated with cotinine (FSA), only 56% of genes were down-regulated (17% decrease). Next, gene expression in the hippocampus of mice that had been subjected to forced swimming and treated with cotinine were compared to the levels present in the hippocampus from stressed mice treated with vehicle. In this comparison, 67% of genes analyzed were up regulated in the hippocampi from cotinine-treated mice when compared to the hippocampal expression in vehicle-treated mice, as seen in FIG. 2.

Using the results from all three comparisons, 15 genes demonstrated differential regulation. Fourteen of these genes were negatively regulated in the stressed mice treated with vehicle, but were positively regulated in stressed mice treated with cotinine. Three genes showed statistically significant differences in expression including Acetylcholinesterase gene (Ache) (p=0.03), ErbB2 (p=0.008) and Vascular endothelial growth factor gene (VEGFa (p=0.03).

In the hippocampus of vehicle treated and stressed mice, the expression of the vascular endothelial growth factor gene, VEGFa, was slightly down-regulated by 1.1-fold compared to mice that were not exposed to stress. However, stressed mice treated with cotinine showed a 1.3-fold up regulation of VEGFa expression when compared to stressed mice treated with vehicle. Also, cotinine induced a highly significant up regulation of the expression of V-erb-b2 erythroblastic leukemia viral oncogene homolog 2 (Errb2) by 1.3 fold in stressed mice compared to stress control mice. By contrast, Errb2 was down-regulated by 1.5 fold in stressed mice treated with vehicle compared to the mice that were not exposed to stress. EGF, the gene that codes for the epidermal growth factor (EGF), is up regulated 1.5-fold in stressed mice treated with cotinine compared to the stressed mice treated with vehicle. Similarly, EGF was down-regulated by 1.5-fold in mice exposed to forced swimming stress treated with vehicle compared to mice that were not exposed to stress. Gdnf, the gene for glial cell line derived neurotrophic factor, was down-regulated in the vehicle-treated mice exposed to forced swimming by 1.4-fold compared to mice that were not exposed to stress, but up regulated 2.0-fold in stressed mice treated with cotinine when compared to stressed mice treated with vehicle. Similarly, Artn, the gene for Artemin, was down-regulated 1.3-fold in the vehicle-treated stressed mice when compared to vehicle-treated mice that were not exposed to stress, but up regulated 1.2-fold in stressed mice treated with cotinine compared to stressed mice treated with vehicle, as seen in Table 2.

TABLE 2

The relative change in neurogenesis gene expression induced by cotinine (Cot), for mice exposed to stress (ES) or not exposed to stress (NES), expressed as fold negative or positive regulation respect to control vehicle-treated.

Figure 3:
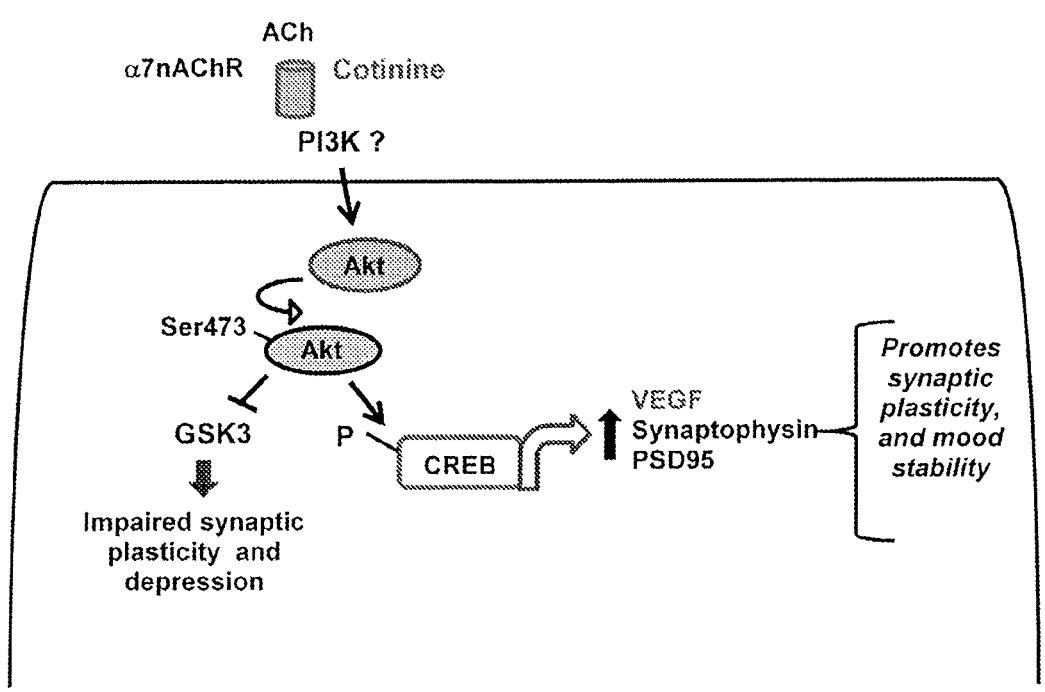
FIG. 3 is a model showing cotinine-based effects on cellular pathways resulting in alterations in neurogenesis genes.

| Gene | RefSeq | ES & NES | p | ES + Cot & NES | p | ES + Cot & NES | p |
|---|---|---|---|---|---|---|---|
| Bmp2a | NM 007553 | −1.5 | 0.0016** | −1.2 | 0.3283 | 1.2 | 0.2193 |
| Erbb2b | NM 001003817 | −1.6 | 0.0065** | −1.2 | 0.0858 | 1.3 | 0.0134* |
| OLIG2c | NM 016967 | −1.3 | 0.0454* | −1.2 | 0.2588 | 1.1 | 0.1321 |
| Rac1d | NM 009007 | 1.2 | 0.0464* | 1.0 | 0.8179 | −1.12 | 0.5227 |
| Sox2e | NM 011443 | −1.2 | 0.0390* | −1.1 | 0.3839 | 1.1 | 0.5227 |
| Stat3f | NM 011486 | −1.1 | 0.0090** | −1.0 | 0.7598 | 1.1 | 0.1732 |
| Vegfa9 | NM 009505 | −1.1 | 2.2515 | 1.2 | 0.0056** | 1.4 | 0.0135* | aBone morphogenetic protein 2A,
bV-erb-b2 erythroblastic leukemia viral oncogene homolog 2,
cOligodendrocyte lineage,
dRAS-related C3 botulinum substrate 1,
eSRY-box containing gene 2,
fSignal transducer and activator of transcription 3,
g Vascular endothelial growth factor
*p ≤ .05
**p ≤ .01
In light of the results, a model was proposed for cotinine treatment as it relates to neurogenesis, as seen in FIG. 3.

Example 4

VEGF, is a neurotrophin that modulates blood flow, angiogenesis (24) and is involved in neurogenesis (Jin, et al., (2002) Vascular endothelial growth factor (VEGF) stimulates neurogenesis in vitro and in vivo. Proc Natl Acad Sci USA, 99, 11946-11950; Fabel, et al., (2003) VEGF is necessary for exercise-induced adult hippocampal neurogenesis. Eur J Neurosci, 18, 2803-2812; Cao, et al., (2004) VEGF links hippocampal activity with neurogenesis, learning and memory. Nat Genet, 36, 827-835). VEGFa mRNA expression RT-PCR assay showed VEGFa up-regulated in the hippocampus of cotinine-treated FS mice when compared to vehicle-treated FS mice (p<0.01). Since cotinine up-regulated VEGF mRNA expression in the hippocampus of FS mice, associated protein expression levels in the hippocampi of the same mice were analyzed using Western blot analysis.

The Western blot analysis investigated the expression of VEGF (FS mice: n=8-10/group; NES mice: n=4-5/group). Following euthanasia, mice were perfused with saline, and brain tissues were rapidly dissected and stored at −80QC, as described in Example 1. Brain tissues were then disrupted by sonication in cold lyses buffer (Cell Signaling Technology, Danver, Mass., USA) containing a complete protease inhibitor cocktail (Roche Molecular Biochemicals). After sonication, brain extracts were incubated on ice for 30 min and centrifuged at 20,000×g for 30 min at 4° C. Protein concentrations of supernatants were measured using the Bio-Rad protein assay (Bio-Rad, Hercules, Calif., USA). Equal amounts of protein were separated by gradient (4-20%), SOS-PAGE, then transferred to nitrocellulose membranes (BA83 0.2 μM; Bio-Rad). The membranes were blocked in TBS with 0.1% Tween 20 (TBST) containing 5% dry skim milk for 1 h. Membranes were incubated with primary antibodies in TBST overnight at 4° C. and with secondary antibodies for 1 h at room temperature (RT) in a blocking buffer. Rabbit polyclonal antibodies directed against VEGF was obtained from Abeam (Cambridge, Mass., USA). A monoclonal antibody directed against β-tubulin (Promega Corporation, Madison, Wis., USA) was used to control protein sample loading and transfer efficiency. Membranes were washed with TBST and incubated with Ll-COR's goat anti-mouse IRDye secondary antibodies (Ll-COR Biosciences, Lincoln, Nebr.) for 1 h at RT, washed with TBST and TBS. Images were acquired using an Odyssey Infrared Imaging System (Ll-COR Biosciences) and analyzed using the NIH Image J software.

To analyze the group and treatment effects, differences between group means in the behavioral analyses were assessed using two-way analysis of variance (ANOVA) and post hoc Tukey test. Student t-test with or without Welch correction was use to compare protein expression data between two groups. Statistical analyses were conducted using statistical software packages (SPSS, Chicago, Ill., USA and GraphPad Prism, San Diego, Calif., USA). For all comparisons, statistical significance was considered with α=0.05.

Figure 4:
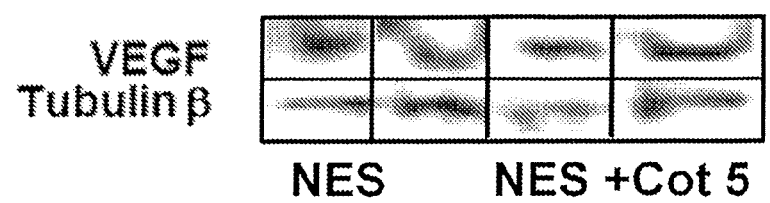
FIG. 4 is a blot showing cotinine increased the expression of VEGF in the hippocampus of mice subjected to repetitive forced swim stress. Mice pretreated with 5 mg/kg of cotinine (Cot 5) or vehicle (Veh) were exposed to repetitive 6-min forced swim (FS) daily for 6 days (a) to under continuous treatment. Following testing, mice were euthanized and the levels of VEGF and β-tubulin in the hippocampus were analyzed by Western blot. The plots represent VEGF immunoreactivity (IR) values in the hippocampus of mice.
Figure 5:
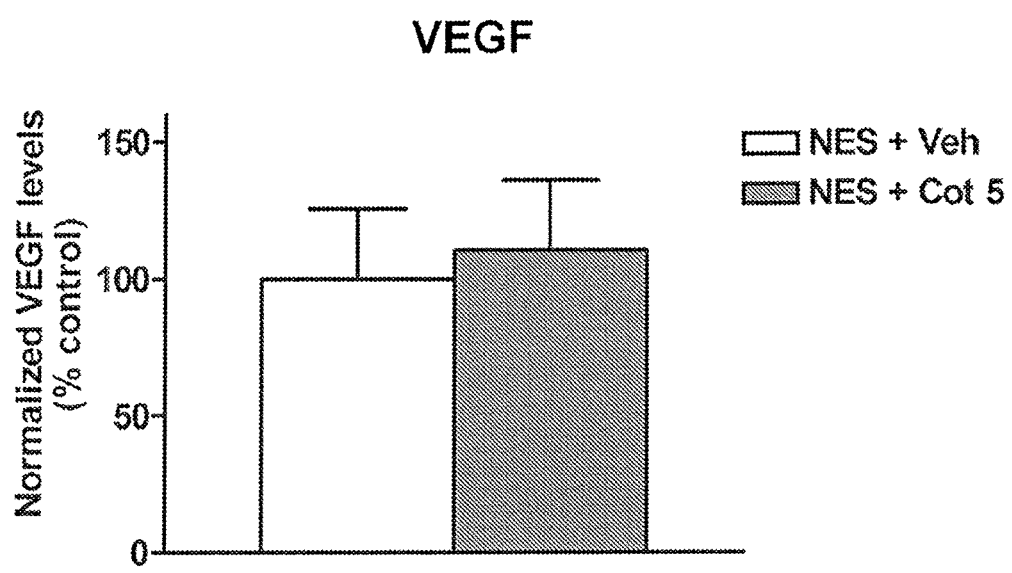
FIG. 5 is a graph showing cotinine increased the expression of VEGF in the hippocampus of mice subjected to repetitive forced swim stress. VEGF immunoreactivity (IR) in the blots from FIG. 4 were normalized to β-tubulin and expressed as percentage of the average value found in vehicle-treated mice. Western blot images are seen beneath each comparison. ns, non-significant differences.
Figure 6:
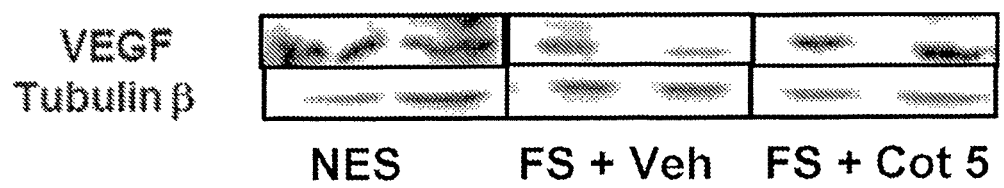
FIG. 6 is a blot showing cotinine increased the expression of VEGF in the hippocampus of mice subjected to repetitive forced swim stress compared to unstressed mice. Mice pretreated with 5 mg/kg of cotinine (Cot 5) or vehicle (Veh) were exposed to repetitive 6-min forced swim (FS) daily for 6 days (a) to under continuous treatment or controls, not subjected to the forced swim (NES). Following resting, mice were euthanized and the levels of VEGF and β-tubulin in the hippocampus were analyzed by Western blot. The plots represent VEGF immunoreactivity (IR) values in the hippocampus of mice.
Figure 7:
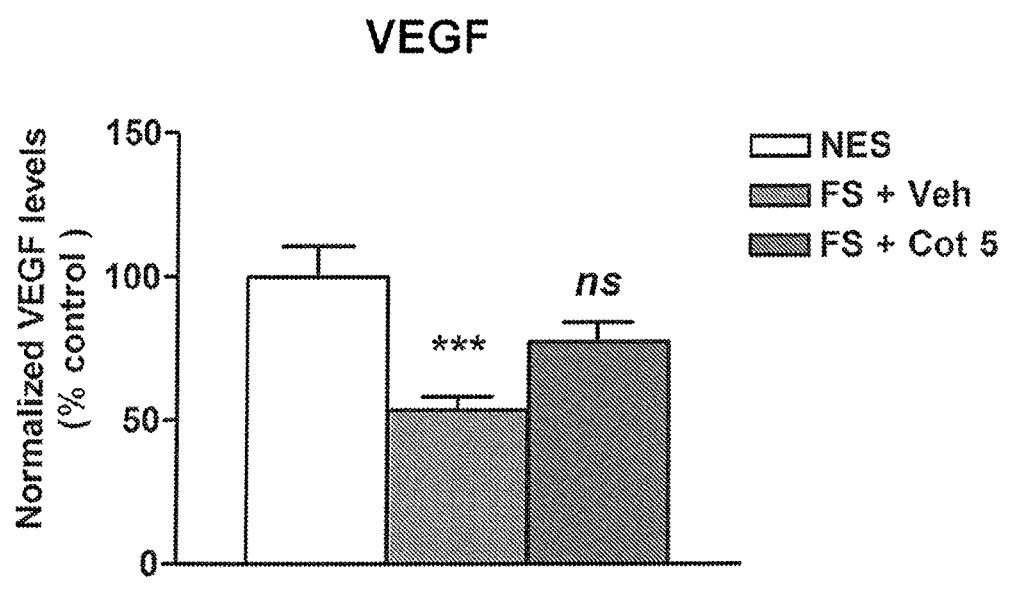
FIG. 7 is a graph showing cotinine increased the expression of VEGF in the hippocampus of mice subjected to repetitive forced swim stress. VEGF immunoreactivity (IR) in the blots from FIG. 6 were normalized to β-tubulin and expressed as percentage of the average value found in vehicle-treated mice. Western blot images are seen beneath each comparison. ns, non-significant differences; ***, $p<0.001$.

After normalization, VEGF staining was shown to be increased in cotinine-treated (5 mg/kg) mice versus vehcile treated mice, as seen in FIG. 4. The results show that the groups differed significantly from one another (F(2,24) =10.19, p=0.0006; FIG. 6 and Tukey-Kramer's post hoc analyses revealed that mice subjected to repetitive FS stress (FIG. 4) had a significant decrease in the expression of VEGF in the hippocampi (p<0.001; FIG. 7. On the other hand, FS mice treated with cotinine showed significantly higher levels of VEGF expression in the hippocampus than vehicle-treated, FS mice, to reach levels not significantly different than those of NES mice (FIG. 7 Finally, in the absence of stress, t-test revealed that cotinine induced no changes in VEGF expression (t=0.2910, p=0.7795; FIG. 5. VEGF is a cytokine that plays an important role modulating neurogenesis and angiogenesis (Schanzer, et al., (2004) Direct stimulation of adult neural stem cells in vitro and neurogenesis in vivo by vascular endothelial growth factor. Brain Pathol, 14, 237-248; Galvan, et al., (2006) The role of vascular endothelial growth factor in neurogenesis in adult brain. Mini reviews in medicinal chemistry, 6, 667-669; Sun, et al., (2006) Vascular endothelial growth factor-B (VEGFB) stimulates neurogenesis: evidence from knockout mice and growth factor administration. Developmental biology, 289, 329-335; Antequera, et al., (2012) Encapsulated VEGFsecreting cells enhance proliferation of neuronal progenitors in the hippocampus of AbetaPP/Ps1 mice. J Alzheimers Dis, 29, 187-200).

It has been found that cotinine, elicits memory enhancing effects (Buccafusco, et al., (2009) Desensitization of nicotinic acetylcholine receptors as a strategy for drug development. J Pharmacol Exp Ther, 328, 364-370; Buccafusco & Terry, (2009) A reversible model of the cognitive impairment associated with schizophrenia in monkeys: potential therapeutic effects of two nicotinic acetylcholine receptor agonists. Biochem Pharmacol, 78, 852-862; Echeverria, et al., (2011 b) Cotinine reduces amyloid-beta aggregation and improves memory in Alzheimer's disease mice. J Alzheimers Dis, 24, 817-835; Echeverria Moran, (2012) Cotinine: Beyond that Expected, More than a Biomarker of Tobacco Consumption. Frontiers in pharmacology, 3, 173) and positive effects on brain plasticity in animal models of behavior. Clinical studies investigated the effect of cotinine at doses up to 1.5 mg cotinine base/kg and found cotinine impaired recall on the long list on a verbal recall task but did not affected the recall of a short list or altered the scores in the profile of mood state (Herzig 1998; McNeil, 1971). Cotinine, in the presence of stress, increases the expression of VEGF, a growth factor important in neurogensis.

Example 5

Figure 8:
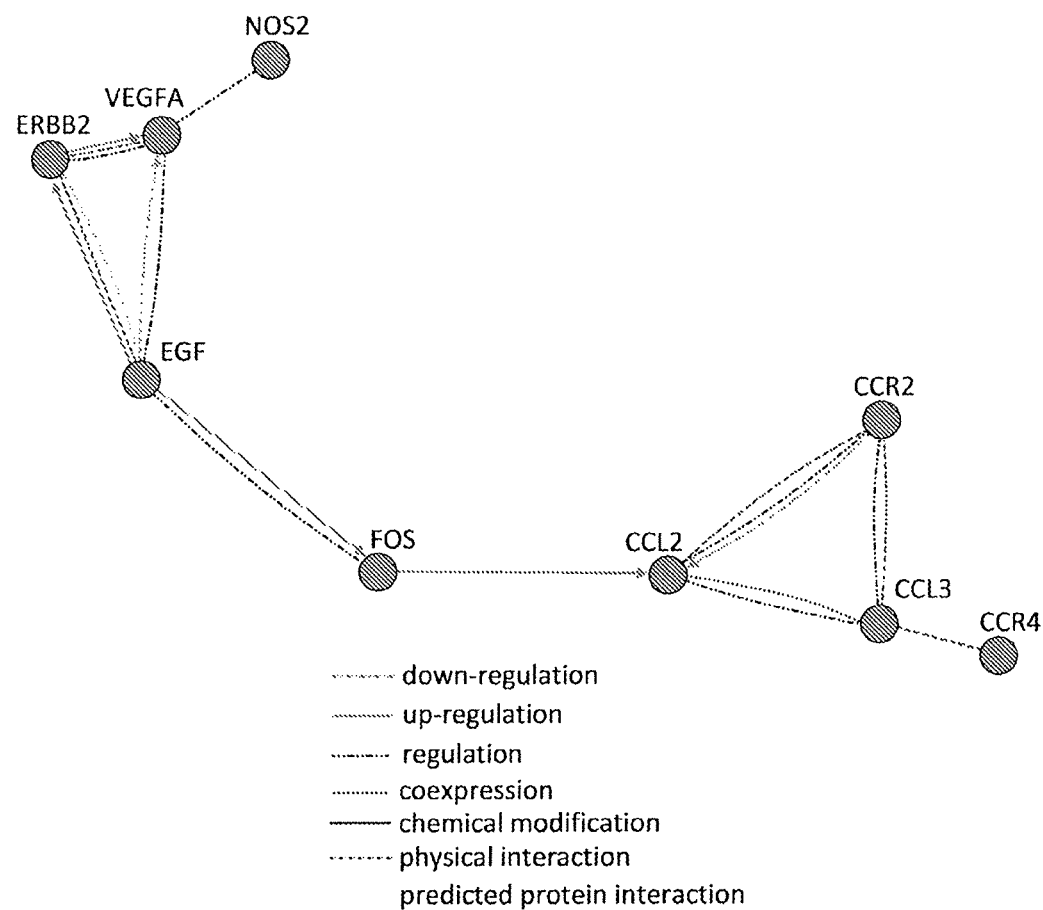
FIG. 8 is a plot of the gene relationships for Ccr4, Ccl3, Ccr2, Ccl2, Fos, Erbb2, EGF, VEGFa and Nos2.

Using the results of Example 2 and Example 3, genes that displayed differential regulation were entered into the Gene Network Central Pro database from SABiosciences to determine any established gene relationship(s) in a Gene Interaction Network. The database uses published literature to establish known gene interactions. The following nine genes were identified to have known interactions: Ccr4, Ccl3, Ccr2, Ccl2, Fos, Erbb2, EGF, VEGFa and Nos2. The results are pictured in FIG. 8.

Cotinine treatment increased neurogenesis-promoting genes, including VEGFa, EGF, Erbb2, Gdnf, and Artn, while decreasing inflammation and oxidation-related genes, such as Nos2, and Fos, and most chemokine genes.

The vascular endothelial growth factor (VEGF)-encoding gene, VEGFa, provides for a neurotrophin that modulates blood flow and angiogenesis (Lee, et al., Induction of Neuronal Vascular Endothelial Growth Factor Expression by cAMP in the Dentate Gyms of the Hippocampus Is Required for Antidepressant-Like Behaviors. The Journal of Neuroscience, 2009. 29(26):8493-8505). Stress has been shown to reduce the expression of VEGFa (Raison, et al., Cytokines sing the blues: inflammation and the pathogenesis of depression. Trends Immunol. 2006 Jan.; 27(1):24-31) and VEGF has previously been implicated in supporting the positive effects of several antidepressants by stimulating the cAMP-CREB (cAMP response element-binding protein) pathway (Lee, et al., Induction of Neuronal Vascular Endothelial Growth Factor Expression by cAMP in the Dentate Gyms of the Hippocampus Is Required for Antidepressant-Like Behaviors. The Journal of Neuroscience, 2009. 29(26):8493-8505). The stimulation of this pathway has been shown to inhibit depressive behavior, decrease neurodegeneration and improve memory (Lee, et al., Induction of Neuronal Vascular Endothelial Growth Factor Expression by cAMP in the Dentate Gyms of the Hippocampus Is Required for Antidepressant-Like Behaviors. The Journal of Neuroscience, 2009. 29(26):8493-8505). In addition, supporting a possible role of VEGF in the actions of cotinine, experiments conducted by Lee et al. demonstrated that increases in VEGF expression stimulated neurogenesis in mice (Lee, et al., Induction of Neuronal Vascular Endothelial Growth Factor Expression by cAMP in the Dentate Gyms of the Hippocampus Is Required for Antidepressant-Like Behaviors. The Journal of Neuroscience, 2009. 29(26):8493-8505). This evidence is consistent with the idea that an increase in VEGF induced by cAMP may underlie the effects of cotinine. All together this evidence supports the hypothesis that an increase of VEGF expression induced by cotinine mediates its effects in the promotion of neurogenesis.

V-erb-b2 erythroblastic leukemia viral oncogene homolog 2 (Erbb2) is a member of the tyrosine kinase family of epidermal growth factors (Impey, et al., Stimulation of cAMP response element (CRE)-mediated transcription during contextual learning. Nat Neurosci. 1998. 1(7):595-601). As a member of the epidermal growth factor family, ErbB2 participates in cell adhesion and promoting vasculature (Yang, ErbB2 Overexpression Correlates with Increased Expression of Vascular Endothelial Growth Factors A, C, and D in Human Breast Carcinoma. CANCER. 2002. 94 (11):2855-61). Interestingly, studies have shown that ErbB2 is commonly up regulated with VEGF (Yang, ErbB2 Overexpression Correlates with Increased Expression of Vascular Endothelial Growth Factors A, C, and D in Human Breast Carcinoma. CANCER. 2002. 94 (11):2855-61). The results herein concurred, showing ErbB2 expression approximated the expression of VEGF. Up regulation of ErbB2 expression has been suggested as a mechanism of promoting neurogenesis by regulating the differentiation of radial glial cells into astrocytes (Ghashghaei, et al., Reinduction of ErbB2 in astrocytes promotes radial glial progenitor identity in adult cerebral cortex, Genes Dev. 2007. 21 (24): 3258-3271). Early in development, radial glial cells transform into astrocytes as ErbB2 expression is down-regulated. (Ghashghaei, et al., Reinduction of ErbB2 in astrocytes promotes radial glial progenitor identity in adult cerebral cortex, Genes Dev. 2007. 21 (24): 3258-3271) In animal studies, re-expression of ErbB2 allowed radial glial to support neuronal migration, a necessary mechanism in neurogenesis (Ghashghaei, et al., Reinduction of ErbB2 in astrocytes promotes radial glial progenitor identity in adult cerebral cortex, Genes Dev. 2007. 21 (24): 3258-3271). ErbB2 has also been implicated in participating in regulator pathways that lead to insulin resistance after induction of cellular stress by administering cytokines in culture. (Hemi, et al., Transactivation of ErbB2 and ErbB3 by tumor necrosis factor-alpha and anisomycin leads to impaired insulin signaling through serine/threonine phosphorylation of IRS proteins. J Biol Chem. 2002 Mar. 15; 277(11):8961-9) Thus, cotinine may also enhance neurogenesis and improve brain homeostasis by up regulating the expression of ErbB2.

Cotinine increased expression of EGF in stress-induced mice, whereas control treatment with vehicle resulted in decreased EGF expression, as discussed in Example 3. This suggests that cotinine can prevent the down regulation of EGF expression induced by stress and further increase its expression. EGF is known to play an important role in neurogenesis by stimulating the differentiation, proliferation and migration of neurons (Tian, et al., A study of the functional significance of epidermal growth factor in major depressive disorder. Psychiatr Genet. 2012. 22(4):161-7). Tian et al demonstrated that plasma EGF levels were decreased in patients with major depressive disorder compared with control patients (Hemi, et al., Transactivation of ErbB2 and ErbB3 by tumor necrosis factor-alpha and anisomycin leads to impaired insulin signaling through serine/ threonine phosphorylation of IRS proteins. J Biol Chem. 2002 Mar. 15; 277(11):8961-9).

As noted in Example 3, expression of both Gdnf (Glial cell line derived neurotrophic factor) and Artn (Artemin) are up regulated in stressed mice treated with cotinine compared to stressed mice treated with vehicle. Gdnf and Artn are both neurtrophins, and members of the GDNF family (Tian, et al., A study of the functional significance of epidermal growth factor in major depressive disorder. Psychiatr Genet. 2012. 22(4):161-7). These neurotrophins exert their action through the GDNF family receptor to activate the tyrosine kinase RET part of signaling pathways involved in cell survival, inflammation differentiation and apoptosis (Tian, et al., A study of the functional significance of epidermal growth factor in major depressive disorder. Psychiatr Genet. 2012. 22(4):161-7). GDNF reduces oxidative stress-induced cell death in cultured neurons and supports the viability of mesencephalic dopaminergic neurons in culture by suppressing apoptosis (Tian, et al., A study of the functional significance of epidermal growth factor in major depressive disorder. Psychiatr Genet. 2012. 22(4):161-7). Administration of cotinine up regulates the expression of Gdnf and Artn and may therefore positively inhibiting oxidative damage of the brain.

Nitric oxide is a free radial which can cause oxidative damage to cells (Zhou, et al., Neuronal nitric oxide synthase contributes to chronic stress-induced depression by suppressing hippocampal neurogenesis. Journal of Neurochemistry. 2007. 103(5):1843-1854), produced by nitric oxide synthase, of which there are three isozymes; neuronal NOS (nNOS), endothelial NOS, (eNOS) and inducible NOS (NOS2) (Zhou, et al., Neuronal nitric oxide synthase contributes to chronic stress-induced depression by suppressing hippocampal neurogenesis. Journal of Neurochemistry. 2007. 103(5):1843-1854). Nitric Oxide Synthase 2 (NOS2) is involved in the deleterious effects of neuroinflammation and oxidative stress (Zhou, et al., Neuronal nitric oxide synthase contributes to chronic stress-induced depression by suppressing hippocampal neurogenesis. Journal of Neurochemistry. 2007. 103(5):1843-1854). There is a correlation between increased levels of nNOS in the brain, decreased neurogenesis and depression (Lucassen, et al., "Regulation of adult neurogenesis by stress, sleep disruption, exercise and inflammation: Implications for depression and antidepressant action." European Neuropsychopharmacology 20.1 (2010): 1-17). Zhou et al showed that mice with a genetic deletion of nNOS or that were treated with nNOS inhibitors showed increased levels of neurogenesis and lower levels of depressive-like behavior (Zhou, et al., Neuronal nitric oxide synthase contributes to chronic stress-induced depression by suppressing hippocampal neurogenesis. Journal of Neurochemistry. 2007. 103(5):1843-1854). These results suggest that cotinine may decrease iNOS expression in the hippocampus. Because of this effect, cotinine may have an anti-oxidant effect contributing to increasing neurogenesis under pathological conditions.

FBJ osteosarcoma oncogene (Fos) is a member of the activator protein 1 (AP1-) family of transcription factors that work in concert with nuclear factor kappa beta (NFkB) to regulate the expression of genes involved in inflammation, oncogenesis and apoptosis (Nadjar, et al., Inactivation of the Cerebral NFkB Pathway Inhibits lnterleukin-1 b-lnduced Sickness Behavior and c-Fos Expression in Various Brain Nuclei. Neuropsychopharmacology. 2005. 30: 1492-1499). It has been demonstrated that c-Fos can be inactivated when the NFkB pathway is blocked (Nadjar, et al., Inactivation of the Cerebral NFkB Pathway Inhibits lnterleukin-1 b-induced Sickness Behavior and c-Fos Expression in Various Brain Nuclei. Neuropsychopharmacology. 2005. 30: 1492-1499). NFkB causes inflammatory damage that allows previously excluded substances to cross the blood-brain barrier when activated by inflammatory cytokines (Nadjar, et al., Inactivation of the Cerebral NFkB Pathway Inhibits lnterleukin-1 b-lnduced Sickness Behavior and c-Fos Expression in Various Brain Nuclei. Neuropsychopharmacology. 2005. 30: 1492-1499). Cotinine decreased the expression of Fos gene in mice exposed to forced swimming. Altogether this evidence indicates that decreasing c-Fos expression via cotinine can alleviate damage induced by neuroinflammation in the brain possibly by disrupting NFkB signaling.

Complement Component 3 (C3) is a component of the innate immune system, which is released by macrophages and acts as a cytokine under inflammatory conditions (Boyle, et al., Hostility, Anger and Depression Predict Increases in C3 over a 10-Year Period. Brain Behav lmmun. 2007. 21 (6): 816-823), and increases under conditions of psychological stress (Boyle, et al., Hostility, Anger and Depression Predict Increases in C3 over a 10-Year Period. Brain Behav lmmun. 2007. 21 (6): 816-823). C3 has also been linked to incidence of cardiovascular diseases including myocardial infarction and stroke and his levels correlate with cardiovascular risk factors including blood pressure, BMI and lipids (Engstrom, et al., Complement C3 and C4 in plasma and incidence of myocardial infarction and stroke: a population-based cohort study. Eur J Cardiovasc Prev Rehabil. 2007. 14(3):392-7). Also, elevated C3 may contribute to dysregulation of the HPA (Zhou, et al., Neuronal nitric oxide synthase contributes to chronic stress-induced depression by suppressing hippocampal neurogenesis. Journal of Neurochemistry. 2007. 103(5):1843-1854).

Five members of the chemokine family were differentially expressed, with some chemokines up regulated by cotinine treatment (Ccl1, Ccl2 and Ccr4) in the mouse exposed to forced swimming when compared to the stressed mouse treated with vehicle. However, most of the cytokines and chemokines were modestly down regulated by cotinine in the stressed mouse. Chemokines are small proteins responsive to basal and inflammatory conditions in the immune system and are constitutively present in glial cells and neurons in the brain (Rostene, et al., Chemokines: a new class of neuromodulator? Nat Rev Neurosci. 2007. 8 (11): 895-903). They are divided into four families based on the configuration of conserved cysteine residues at their amino terminus as follows: CXC, CC, C and CX3C (Rostene, et al., Chemokines: a new class of neuromodulator? Nat Rev Neurosci. 2007. 8 (11):895-903). All of the chemokines we observed to be differentially expressed belong to the CC, or beta family, which chemoattract monocytes, macrophages, basophils, T lymphocytes and eosinophils (Rostene, et al., Chemokines: a new class of neuromodulator? Nat Rev Neurosci. 2007. 8 (11): 895-903).

Monocyte chemoattractant protein (CC12) is up regulated under neuroinflammatory conditions and Ccr2 is its receptor (Rostene, et al., Chemokines: a new class of neuromodulator? Nat Rev Neurosci. 2007. 8 (11):895-903). Ccl2 is highly expressed in various brain tissues including the pituitary gland, glial cells and neuronal cells in rat brains and human cell lines, while Ccr2 is expressed in the spinal cord and neurons in the rat brain (Rostene, et al., Chemokines: a new class of neuromodulator? Nat Rev Neurosci. 2007. 8 (11): 895-903). While initial evidence demonstrated only the immune effects of chemokines, some studies have implicated chemokine as neurotransmitters or neuromodulators (Rostene, et al., Chemokines: a new class of neuromodulator? Nat Rev Neurosci. 2007. 8 (11):895-903). Ccl2 is colocalized with cholinergic neurons and dopaminergic neurons indicating that it may be involved in neurotransmission (Rostene, et al., Chemokines: a new class of neuromodulator? Nat Rev Neurosci. 2007. 8 (11):895-903). Additionally, Ccl2 reduces, in a dose dependent manner, the GABA-induced electrical responses in rat cultured neurons (Minami, et al., Brain Cytokines and Chemokines: Roles in lschemic Injury and Pain. J Pharmacol Sci (2006). 100, 461-470). It has been reported that the antagonism of the Ccr2 receptor reduced neuroinflammation in rodent models of multiple sclerosis and inflammatory arthritis (Minami, et al., Brain Cytokines and Chemokines: Roles in lschemic Injury and Pain. J Pharmacol Sci (2006). 100, 461-470). We found a marked down regulation of Ccr2 by cotinine in the stressed mice even though we observed an increase in the ligand Ccl2.

Macrophage inflammatory protein (Ccl3), is a proinflammatory chemokine involved in monocyte and microglia activation and migration (Minami, et al., Brain Cytokines and Chemokines: Roles in lschemic Injury and Pain. J Pharmacol Sci (2006). 100, 461-470). In animal studies, using LPS, a known cytokine stimulant, concentrations of Ccl3 were increased (Brown, et al., Production of Proinflammatory Cytokines and Chemokines during Neuroinflammation: Novel Roles for Estrogen Receptors α and β. Endocrinology. 2010 October; 151(10)). A known anti-inflammatory, estradiol-17, was unable to lower the levels of Ccl3 in these studies (Brown, et al., Production of Proinflammatory Cytokines and Chemokines During Neuroinflammation: Novel Roles for Estrogen Receptors α and β. Endocrinology. 2010 October; 151(10)). Elevated Ccl3 levels have also been linked to depression (Brown, et al., Production of Proinflammatory Cytokines and Chemokines During Neuroinflammation: Novel Roles for Estrogen Receptors α and β. Endocrinology. 2010 October; 151(10)). One study measured blood serum levels of Ccl3 in healthy donors and patients with moderate to severe depression and found that Ccl3 was detectable in 20% of depressed patients but absent in healthy donors (Brown, et al., Production of Proinflammatory Cytokines and Chemokines During Neuroinflammation: Novel Roles for Estrogen Receptors α and β. Endocrinology. 2010 October; 151(10)). As previously stated, inflammation can be a beneficial mechanism, but if left unchecked it can become damaging.

These results suggest that cotinine may decrease the expression of these neuroinflammatory factors, especially if tested in a different animal model of stress that would induce higher levels of neuroinflammation.

The data herein suggests that cotinine may be a good candidate for neurogenesis pharmacotherapy, during highly stressful life events. Cotinine is a positive allosteric modulator (PAM) of the homomeric α7 nAChR (Moran, (2012) Cotinine: Beyond that Expected, More than a Biomarker of Tobacco Consumption. Frontiers in pharmacology, 3, 173). New evidence in vivo suggests that cotinine's effects are mediated by α7 and α4β2 nAChRs (Aguiar, et al., (2013) Neuroactive effects of cotinine on the hippocampus: Behavioral and biochemical parameters. Neuropharmacology, 71, 292-298; Wildeboer-Andrud, et al., (2014) Cotinine impacts sensory processing in DBA/2 mice through changes in the conditioning amplitude. Pharmacol Biochem Behav, 117, 144-150). Deleterious effects of stress result, at least in part, from a deregulation of the central monoamine systems. Cotinine increase the release and reduce the uptake of 5-HT in the brain of rats (Fuxe, et al., (1979) On the action of nicotine and cotinine on central 5-hydroxytryptamine neurons. Pharmacol Biochem Behav, 10, 671-677). Further, cotinine up-regulated hippocampal VEGF expression in the FS mice, as well as other neurogenesis genes. Stress reduces hippocampal neurogenesis (Gould & Tanapat, (1999) Stress and hippocampal neurogenesis. Biol Psychiatry, 46, 1472-1479) and the enhancement of hippocampal neurogenesis buffers the stress response as well as depressive-like behavior (Snyder, et al., (2011) Adult hippocampal neurogenesis buffers stress responses and depressive behaviour. Nature, 476, 458-461). Furthermore, several commonly prescribed antidepressants stimulate the expression of neurogenesis genes (Newton & Duman, (2004) Regulation of neurogenesis and angiogenesis in depression. Current neurovascular research, 1, 261-267; Fournier & Duman, (2012) Role of vascular endothelial growth factor in adult hippocampal neurogenesis: implications for the pathophysiology and treatment of depression. Behav Brain Res, 227, 440-449).

VEGF is neuroprotective (Gora-Kupilas & Josko, (2005) The neuroprotective function of vascular endothelial growth factor (VEGF). Folia neuropathologica I Association of Polish Neuropathologists and Medical Research Centre, Polish Academy of Sciences, 43, 31-39) and positively influences neurite outgrowth (Jin, et al., (2006) Vascular endothelial growth factor stimulates neurite outgrowth from cerebral cortical neurons via Rho kinase signaling. J Neurobiol, 66, 236-242). For example, increased VEGF levels prevent motor neuron degeneration induced by expression of a mutant form of the superoxide dismutase 1 (Lunn, et al., (2009) Vascular endothelial growth factor prevents G93A-SOD1-induced motor neuron degeneration. Developmental neurobiology, 69, 871-884). Furthermore, environmental enrichment, considered of therapeutic value against depression (Hannan, (2014) Environmental enrichment and brain repair: harnessing the therapeutic effects of cognitive stimulation and physical activity to enhance experience-dependent plasticity. Neuropathol Appl Neurobiol, 40, 13-25), enhances neurogenesis as well as hippocampal VEGF levels (Cao, et al., (2004) VEGF links hippocampal activity with neurogenesis, learning and memory. Nat Genet, 36, 827-835). Moreover, increases in VEGF expression stimulate adult hippocampal neurogenesis (Fournier & Duman, (2012) Role of vascular endothelial growth factor in adult hippocampal neurogenesis: implications for the pathophysiology and treatment of depression. Behav Brain Res, 227, 440-449).

While our observation that cotinine treatment alters VEGF in the hippocampus is novel, an arterial epitheial cell study showed nicotine- and cotinine-induced cellular change in mRNA VEGF expressio (Conklin, et al., (2002) Nicotine and cotinine up-regulate vascular endothelial growth factor expression in endothelial cells. Am J Pathol, 160, 413-418). In neurons, cotinine prevented the decrease in the expression of VEGF in the hippocampus of the mice exposed to repetitive FS stress. Interestingly, cotinine did not change VEGF protein levels in non-stressed mice. Therefore, it is unlikely that cotinine is influencing VEGF expression directly, but exerts its effects in the presence of stress, likely through a facilitation of molecular mechanisms of homeostasis. Altogether cotinine promotes restorative cerebral changes by stimulating signaling factors such as VEGF, which may, in turn, promote plasticity processes such as neurogenesis. Given cotinine has good pharmacokinetic properties (De Schepper, et al., (1987) Kinetics of cotinine after oral and intravenous administration to man. European journal of clinical pharmacology, 31, 583-588) and a positive safety profile in humans, which includes no habit-forming properties or withdrawal effects, among others (Hatsukami, et al., (1997) Safety of cotinine in humans: physiologic, subjective, and cognitive effects. Pharmacol Biochem Behav, 57, 643-650; Hatsukami, et al., (1998a) Effects of cotinine on cigarette self-administration. Psychopharmacology (Berl), 138, 184-189; Hatsukami, et al., (1998b) Cotinine: effects with and without nicotine. Psychopharmacology (Berl), 135, 141-150; Echeverria Moran, (2012) Cotinine: Beyond that Expected, More than a Biomarker of Tobacco Consumption. Frontiers in pharmacology, 3, 173.), cotinine therapeutic intervention during stress is useful in increasing neurogenesis, enhancing synaptic plasticity, learning and memory, and the expression of neurogenesis factors such as VEGF during stress and neurodegenerative conditions.

In preceding specification, all documents, acts, or information disclosed does not constitute an admission that the documents, act, or information of any combination thereof was publicly available, known to the public, part of the general knowledge in the art, or was known to be relevant to solve any problem at the time of priority.

The disclosures of all publications cited above are expressly incorporated herein by reference each, Example 6

Materials and Methods

Animals

Wistar female rats (2-4 months of age, 200-300 g) (n=10/group) were obtained from Harlan laboratories. Rats were housed in pairs, kept at 12 h light/12 h dark cycle and maintained in an air-conditioned room at a temperature of 21±1° C. and relative humidity of 60±10%. Food and water were available ad libitum. All rats were acclimated to the Veterinary Medical Unit for 1 week and handled daily. Weight was recorded every 2 days to assess for dehydration induced by the chemotherapy regime. All procedures were approved by the Institutional Animal Care and Use (IACUC) committee of the Bay Pines Veterans Affairs (VA) Healthcare System, in accordance with VA and The Guide for the Care and Use of Laboratory Animals.

Administration of Drugs Schedule

Cotinine [(5S)-1-methyl-5-(3-pyridyl)-pyrrolidin-2-one] was obtained from Sigma-Aldrich (Saint Louis, Mo.). Chemotherapy drugs were provided by the Bay Pines VA pharmacy.

Following the habituation period, rats were divided into 4 groups (n=6-12/condition) and treated with warm saline (vehicle) or a combination of cyclophosphamide (40 mg/kg), methotrexate (37.5 mg/kg) and 5-fluorouracil (75 mg/kg) (CMF) via intraperitoneal (i.p. or IP) injection once a week for 2 weeks, the shortest time inducing cognitive impairment in the rats. The doses were chosen based on previous protocols inducing cognitive impairment in rats (Briones T L, Woods J (2011) Chemotherapy-induced cognitive impairment is associated with decreases in cell proliferation and histone modifications. BMC Neurosci 12:124). Three days after chemotherapy, rats started daily treatment with cotinine (5 mg/kg) (Cot 5) or vehicle (saline) (FIG. 9a). Post-treatment with cotinine and/or vehicle was administered via oral administration of 50 μl solutions, using gavage syringes in the mouse, 30 min prior to behavioral testing and throughout the testing period until euthanasia. During the chemotherapy regime, the diet of rats was supplemented with an electrolyte solution containing (45 mEq/L sodium, 20 mEq/L potassium, 7.8 mg/L zinc, 35 mg/L chloride and 2% dextrose) as needed to diminish weight loss.

Behavioral Analysis

Novel Location Recognition Test (NOL).

This task evaluates spatial recognition memory and is based on the preferential exploration of a displaced object by rodents able to detect a novel placement of an object after remembering each object's original positions (Ennaceur A, Delacour J (1988) A new one-trial test for neurobiological studies of memory in rats. 1: Behavioral data. Behav Brain Res 31(1):47-59). In this task after habituation, and during the familiarization phase, two identical objects were placed at equidistant positions within the testing arena. Rats were allowed to explore the objects freely for 3 min (min). After a 7-min resting period in their cages, rats were returned to the arena where the same objects from the previous step were present, one in the same location and one in a different location. The discrimination index (DI), which is a measure of spatial recognition memory, was calculated as follows: time spent exploring the object in the new location/total time spent exploring both objects.

Porsolt's Forced Swim Test.

This task was chosen to determine the effect of cotinine on depressive-like behavior is one of the more broadly used to assess potential antidepressant effects of drugs (Porsolt R D, Bertin A, Jalfre M (1977) Behavioral despair in mice: a primary screening test for antidepressants. Arch Int Pharmacodyn Ther 229(2):327-336; Castagne V, Moser P, Roux S, Porsolt R D (2010) Rodent models of depression: forced swim and tail suspension behavioral despair tests in rats and mice. Curr Protoc Neurosci 49:5.8.1-5.8.14). Each rat was placed in a transparent cylinder filled with water at room temperature (25° C.). The freezing behavior, during 6-min trials, was recorded on video and scored by investigators blinded to the treatment arms. The immobility (freezing) time was recorded during a 6-min forced swim (FS) trial. A rat was considered immobile when it remained floating motionless in the water and moving only to keep its head above the water. The time in seconds (sec) spent by the mice immobile was scored by two investigators blind to the mice's treatments. Time freezing is considered a measure of depressive behavior in rats.

Rotarod.

The rotarod test was used to assess sensorimotor abilities and locomotor activity (Jones B J, Roberts D J (1968) A rotarod suitable for quantitative measurements of motor incoordination in naive mice. Naunyn Schmiedebergs Arch Exp Pathol Pharmakol 259(2):211). Motor behavioral performance was determined in a rotarod apparatus (Panlab, Barcelona, Spain) in which the time each rat stays on the rotarod at accelerating speed from 4 to 40 revolutions per minute (rpm) was measured. Rats were tested in 3 trials per day (5 min each, separated by a 30 min rest period) for 2 consecutive days.

Statistical Analysis

Differences among the means were analyzed using one-way analysis of variance (ANOVA). Student's t test and the post hoc multiple comparisons Tukey's tests were used when required. Welch's correction was used when non-equal variances were observed. Statistical significance was considered with $p<0.05$.

To test our hypothesis that cotinine, by positively modulating the α7nAChR, may diminish the deleterious neurological effects of chemotherapy, we used a rodent model to study chemotherapy-induced side effects. Rodent models have been useful to test chemotherapy-induced side effects. For example, rodents treated with cyclophosphamide (Macleod J E, DeLeo J A, Hickey W F, Ahles T A, Saykin A J, Bucci D J (2007) Cancer chemotherapy impairs contextual but not cue-specific fear memory. Behav Brain Res 181(1):168-172), methotrexate (Lyons L, ElBeltagy M, Umka J, Markwick R, Startin C, Bennett G, Wigmore P (2011) Fluoxetine reverses the memory impairment and reduction in proliferation and survival of hippocampal cells caused by methotrexate chemotherapy. Psychopharmacology 215(1):105-115) and fluorouracil (CMF) (Lyons L, ElBeltagy M, Bennett G, Wigmore P (2012) Fluoxetine counteracts the cognitive and cellular effects of 5-fluorouracil in the rat hippocampus by a mechanism of prevention rather than recovery. PLoS ONE 7(1):e30010), alone or in combination, develop cognitive deficits mimicking those observed in cancer survivors. To investigate our hypothesis, we tested the effect of cotinine on cognitive abilities and depressive-like behavior in rats treated with CMF. We have chosen CMF for our studies because this combination is used in patients with cancer and induces cognitive deficits in both rats (Briones T L, Woods J (2011) Chemotherapy-induced cognitive impairment is associated with decreases in cell proliferation and histone modifications. BMC Neurosci 12:124) and humans (Schagen S B, van Dam F S, Muller M J, Boogerd W, Lindeboom J, Bruning P F (1999) Cognitive deficits after postoperative adjuvant chemotherapy for breast carcinoma. Cancer 85(3):640-650). A clinical study analyzing breast cancer survivors, 20 years after being treated with CMF, showed that they performed worse, on average, on several neuropsychological tests than random population controls (Koppelmans V, Breteler M M, Boogerd W, Seynaeve C, Schagen S B (2013) Late effects of adjuvant chemotherapy for adult onset non-CNS cancer; cognitive impairment, brain structure and risk of dementia. Crit Rev Oncol Hematol 88(1):87-101). A recent study showed that CMF impaired learning and memory in Wistar rats, providing a model of chemotherapy-induced cognitive impairment (Briones T L, Woods J (2011) Chemotherapy-induced cognitive impairment is associated with decreases in cell proliferation and histone modifications. BMC Neurosci 12:124).

Example 7

Results

Cotinine Stimulated Weight Regain and Reduced Depressive Like Behavior in Rats Subjected to Chemotherapy One-way analysis of weight gain during the 30 days of experiments in all treatment groups, showed a significant main effect of both treatment [$F(2, 30)=26.49$; $p<0.0001$] and time [$F(2, 30)=2.348$; $p=0.0144$] on weight gain between groups. Also a significant interaction between factors was observed [$F(2,30)=2.07$; $p=0.0019$]. Rats treated with chemotherapy showed a marked loss of weight after the second chemotherapy injection. A Post hoc Tukey's analysis showed that cotinine enhanced the recovery of weight gain in the chemotherapy-treated rats, which reached weight levels indistinguishable from the vehicle-treated rats and significantly different from the chemotherapy-treated control rats ($p<0.05$; FIG. 9b).

One-way ANOVA of the results from 2 days of testing showed no significant changes in motor function between vehicle and chemotherapy-treated rats [$F(2, 109)=1.602$, $p>0.05$; FIG. 9c].

One-way ANOVA analysis of differences in depressive-like behavior in the Porsolt's test revealed that one month after the last chemotherapy injection there were significant differences between treatment groups in depressive-like behavior [$F(3,23)=12.04$, $p<0.0001$]. Three weeks after chemotherapy, no significant differences in depressive-like behavior were found between chemotherapy- and vehicle-treated rats ($p>0.05$). However, rats from both cotinine-treated groups showed a significant reduction on depressive-like behavior when compared to the vehicle-treated rats (vehicle-treated vs cotinine-treated, $p<0.001$; chemotherapy-treated vs chemotherapy and cotinine-treated rats, $p<0.01$, FIG. 9d).

Example 8

Effect of Cotinine on Working Memory in Rats Subjected to Chemotherapy

To investigate the effect of cotinine on working memory after chemotherapy, rats were tested in the NOL task. In this task, during the familiarization step, rats investigated both objects in similar percentage. However, in the location recognition step, significant differences between treatment groups were found [$F(3, 21)=4.585$, $p<0.0128$]. Rats subjected to chemotherapy did significantly worse than control rats, showing a lower discrimination index and lower preference to explore the object in the new location ($p<0.05$, FIG. 10b). However, cotinine restored the ability of the rats subjected to chemotherapy to discriminate between the old and new location of the objects, at a level indistinguishable from control rats ($p>0.05$).

Example 9

Discussion

Treatment of cancer is associated with cognitive and mood disturbances. The importance of accurate detection and treatment of depression in patients with cancer and cancer survivors are recognized and extensively investigated; however, several therapeutic questions remain unanswered. It has been observed in a vast majority of cancer patients that depressive behavior interferes with patients' compliance with cancer treatment (Ayres A, Hoon P W, Franzoni J B, Matheny K B, Cotanch P H, Takayanagi S (1994) Influence of mood and adjustment to cancer on compliance with chemotherapy among breast cancer patients. J Psychosom Res 38(5):393-402). {We have recently shown that cotinine prevented depressive-like behavior induced by stress and promoted and/or preserved synaptogenesis in mice (Grizzell J A, Iarkov A, Holmes R, Mori T, Echeverria V (2014) Cotinine reduces depressive-like behavior, working memory deficits, and synaptic loss associated with chronic stress in mice. Behav Brain Res 268:55-65).} In this study, we investigated the effect of post-treatment with cotinine on the behavioral side effects such as cognitive impairment and depressive-like behavior induced by chemotherapy.

To minimize the systemic toxic effects of chemotherapy, we used two sessions of chemotherapy injections instead of four previously reported. The investigation of motor function after chemotherapy, in an accelerated rotarod test, did not show a significant long-lasting impairment in motor function induced by the chemotherapy in the female rats. The time reduction in the chemotherapy regime and the resting period before behavioral testing may explain why we did not observe differences in motor function, between chemotherapy- and vehicle-treated rats. The absence of an effect of cotinine on motor function in the rats was in agreement with our previous reports showing no effect of cotinine on motor function in mice (Zeitlin R, Patel S, Solomon R, Tran J, Weeber E J, Echeverria V (2012) Cotinine enhances the extinction of contextual fear memory and reduces anxiety after fear conditioning. Behav Brain Res 228(2):284-293). Nevertheless, we observed a significant reduction in weight and spatial working memory in rats after chemotherapy that were treated with cotinine.

Chemotherapy-induced cognitive impairment is an important problem in cancer survivors. Current reports on cognition and chemotherapy are contradictory and scarce (Fremouw T, Fessler C L, Ferguson R J, Burguete Y (2012) Preserved learning and memory in mice following chemotherapy: 5-Fluorouracil and doxorubicin single agent treatment, doxorubicin-cyclophosphamide combination treatment. Behav Brain Res 226(1):154-162; Fardell J E, Vardy J, Johnston I N (2013) The short and long term effects of docetaxel chemotherapy on rodent object recognition and spatial reference memory. Life Sci 93(17):596-604). We found that cotinine improved working memory performance and induced a faster weight recovery in the chemotherapy-treated rats when compared to vehicle-treated rats. These results are in agreement with previous reports showing that cotinine improved memory in rodents and primates (Grizzell J A, Echeverria V (2015) New insights into the mechanisms of action of cotinine and its distinctive effects from nicotine. Neurochem Res 40:2032-2046). This improvement may be the result of positive changes induced by cotinine on attention, brain plasticity and/or motivation after chemotherapy.

At the molecular level, the beneficial effects of cotinine are likely the result of the modulation of the α7nAChR. Consistent with the activation of the nAChRs, cotinine has anti-inflammatory (Matsunaga M, Isowa T, Yamakawa K, Fukuyama S, Shinoda J, Yamada J, Ohira H (2014) Genetic variations in the human cannabinoid receptor gene are associated with happiness. PLoS ONE 9(4):e93771; Rehani K, Scott D A, Renaud D, Hamza H, Williams L R, Wang H, Martin M (2008) Cotinine-induced convergence of the cholinergic and PI3 kinase-dependent anti-inflammatory pathways in innate immune cells. Biochim Biophys Acta 1783 (3):375-382) and neuroprotective effects (J. GAO B-LA, J. M. CHAPMAN, D. BERTRAND, A. V. TERRY; (2012) Neuroprotective effects of the nicotine metabolite, cotinine, and several structural analogs of cotinine Paper presented at the Society for Neuroscience, New Orleans). A previous study showed that cotinine reduced the inflammatory response to gram-negative bacteria in monocytes by decreasing the expression of cytokines such as TNF-α, IL-1β and IL-6. This effect of Cotinine was α7nAChR-dependent.

Impaired brain plasticity, poor dendritic arborization and synaptic loss have been implicated in the onset and progression of depression. More importantly for this study, memory impairment seen in rats treated with CMF was associated with a decrease in cell proliferation and synaptic density in the hippocampus. We have previously showed that cotinine-induced antidepressant and memory-enhancing effects in rodents subjected to chronic restraint stress. Thus, it is reasonable to suggest that cotinine may also prevent synaptic loss induced by chemotherapy.

The study of cotinine to treat neurological disorders in cancer survivors may seem paradoxical as some evidence has linked nicotine to carcinogenesis (Wong H P, Yu L, Lam E K, Tai E K, Wu W K, Cho C H (2007) Nicotine promotes colon tumor growth and angiogenesis through beta-adrenergic activation. Toxicol Sci 97(2):279-287). However, cotinine and its derivatives have very distinctive properties to nicotine (Grizzell J A, Echeverria V (2015) New insights into the mechanisms of action of cotinine and its distinctive effects from nicotine. Neurochem Res 40:2032-2046) and have shown no genotoxic effects when tested in both the Salmonella mutagenicity (0-1000 μg/plate) and the Chinese hamster ovary sister chromatid exchange (SCE) (0-1000 μg/ml) (Doolittle D J, Winegar R, Lee C K, Caldwell W S, Hayes A W, de Bethizy J D (1995) The genotoxic potential of nicotine and its major metabolites. Mutat Res 344(3-4): 95-102) genotoxicity assays. Another study investigating the effect of cotinine on tumor development in F344 rats treated with N-[4-(5-nitro-2-furyl)-2-thiazolyl] formamide (FANFT) for 6 weeks, showed that FANFT administration increased the incidences of mesothelioma of the peritoneum and thyroid tumors (LaVoie E J, Shigematsu A, Rivenson A, Mu B, Hoffmann D (1985) Evaluation of the effects of cotinine and nicotine-N'-oxides on the development of tumors in rats initiated with N-[4-(5-nitro-2-furyl)-2-thiazolyl]formamide. J Nat Cancer Inst 75(6):1075-1081). Cotinine, administered in the drinking water for 78 weeks, was neither carcinogenic nor promoted urinary bladder tumors in rats initiated with FANFT.

Interestingly, in vitro, cotinine inhibits enzymes involved in the synthesis of estrogen by inhibiting the enzymes, aromatase and 17-ketosteroid reductase (Barbieri R L, Gochberg J, Ryan K J (1986) Nicotine, cotinine, and anabasine inhibit aromatase in human trophoblast in vitro. J Clin Invest 77(6):1727-1733). These effects, if true also in humans, may have a prophylactic value in persons susceptible to estrogen-dependent tumorigenesis.

Altogether, we postulate that cotinine may be useful in promoting restorative cerebral changes in patients treated with chemotherapy drugs by decreasing neuroinflammation, and facilitating brain plasticity, further studies are under way to investigate the molecular mechanisms underlying the positive effects of cotinine in diminishing chemotherapy-induced neurological side effects.

CONCLUSIONS

There is an increasing recognition of the importance of the management of psychiatric and cognitive sequelae experienced by patients after chemotherapy. This data provides the use of cotinine for treating the neuropsychological side effects of chemotherapy. Cotinine has several advantages when compared to currently used antidepressants and cognitive enhancers such as the SSRI and acetylcholinesterase inhibitors, respectively. The main potential advantages would include having a dual neurological effect in diminishing both depressive behavior and cognitive impairment with a low toxicity profile.

In preceding specification, all documents, acts, or information disclosed does not constitute an admission that the documents, act, or information of any combination thereof was publicly available, known to the public, part of the general knowledge in the art, or was known to be relevant to solve any problem at the time of priority.

The disclosures of all publications cited above are expressly incorporated herein by reference each, in its entirety, to the same extent as if each were incorporated by reference individually.

While there has been described and illustrated specific embodiments of a method of treating chemotherapy-related side effects or stress-related neuroinflammation, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

What is claimed is:

1. A method of reducing chemotherapy-induced cognitive dysfunction comprising administering a therapeutically effective amount of cotinine to a cancer patient experiencing chemotherapy-induced cognitive dysfunction, wherein the therapeutically effective amount of cotinine is about 0.1 mg/kg to about 10 mg/kg.

2. The method of claim 1, wherein the cognitive dysfunction includes memory loss and/or depression.

3. A method of reducing chemotherapy-induced memory loss or depression comprising administering a therapeutically effective amount of cotinine to a cancer patient experiencing chemotherapy-induced memory loss or depression, wherein the therapeutically effective amount of cotinine is about 0.1 mg/kg to about 10 mg/kg.

4. The method of claim 3, wherein administration of the therapeutically effective amount of cotinine to the cancer patient enhances the recovery of chemotherapy-induced weight loss.

5. The method of claim 3, wherein administration of the therapeutically effective amount of cotinine to the cancer patient restores weight.

6. The method of claim 5, wherein weight is restored at a rate faster than in absence of cotinine.

7. The method of claim 5, wherein weight is restored to a greater extent or higher level than in absence of cotinine.

8. The method of claim 3, wherein the cotinine is administered intramuscularly, intraperitoneally or orally.

9. The method of claim 3, wherein the cotinine is administered at the same time, before or after administration of a chemotherapeutic agent.

10. The method of claim 3, wherein the cotinine is administered by the same route as a chemotherapeutic agent.

11. The method of claim 3, wherein the therapeutically effective amount of cotinine modulates energy balance in a cancer patient afflicted with chemotherapy-induced weight loss.

12. The method of claim 3, wherein weight is restored to a weight prior to administration of a chemotherapeutic agent used to treat cancer in a cancer patient subjected to chemotherapy.

13. A method of reducing chemotherapy-induced memory loss or depression comprising administering a therapeutically effective amount of cotinine to a cancer patient prior to chemotherapy or prior to onset of chemotherapy-induced memory loss or depression, wherein the therapeutically effective amount of cotinine is about 0.1 mg/kg to about 10 mg/kg.

14. The method of claim 13, wherein administration of the therapeutically effective amount of cotinine to the cancer patient reduces chemotherapy-induced weight loss or gain in the cancer patient.

15. The method of claim 14, wherein the chemotherapy-induced weight loss is between 8% to 15% body weight in the cancer patient prior to the administration of the therapeutically effective amount of cotinine.

16. The method of claim 13, wherein administration of the therapeutically effective amount of cotinine to the cancer patient maintains the cancer patient's weight.

17. The method of claim 13, wherein weight is maintained to a level higher with cotinine administration than without cotinine administration in a cancer patient treated with a chemotherapeutic agent for the cancer.

18. The method of claim 16, wherein the cotinine is administered during the course of chemotherapy.

* * * * *